US006759573B2

(12) United States Patent
Olhoft et al.

(10) Patent No.: US 6,759,573 B2
(45) Date of Patent: Jul. 6, 2004

(54) METHOD TO ENHANCE AGROBACTERIUM-MEDIATED TRANSFORMATION OF PLANTS

(75) Inventors: Paula Olhoft, Roseville, MN (US); David A. Somers, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 213 days.

(21) Appl. No.: 09/738,398

(22) Filed: Dec. 15, 2000

(65) Prior Publication Data

US 2001/0034888 A1 Oct. 25, 2001

Related U.S. Application Data

(60) Provisional application No. 60/170,981, filed on Dec. 15, 1999, and provisional application No. 60/224,715, filed on Aug. 11, 2000.

(51) Int. Cl.$^7$ ............................ A04L 5/00; C12N 15/82; C12N 15/87; C12N 5/10; C07H 21/04
(52) U.S. Cl. ....................... 800/294; 800/278; 800/298; 800/312; 536/23.1; 435/419
(58) Field of Search ................................. 800/294, 278, 800/298, 312; 536/23.1; 435/419

(56) References Cited

U.S. PATENT DOCUMENTS

| | | | | |
|---|---|---|---|---|
| 4,992,375 | A | 2/1991 | Wright | 435/240.5 |
| 5,169,770 | A | 12/1992 | Chee et al. | 435/172.3 |
| 5,244,802 | A | 9/1993 | Rangan | 435/240.5 |
| 5,268,463 | A | 12/1993 | Jefferson | 536/23.7 |
| 5,322,783 | A | 6/1994 | Tomes et al. | 435/172.1 |
| 5,376,543 | A | 12/1994 | Chee et al. | 435/172.3 |
| 5,416,011 | A | 5/1995 | Hinchee et al. | 435/172.3 |
| 6,162,965 | A | 12/2000 | Hansen | 800/278 |
| 6,329,571 | B1 | 12/2001 | Hiei | |
| 6,353,155 | B1 | 3/2002 | Kloti et al. | |

FOREIGN PATENT DOCUMENTS

| | | | | |
|---|---|---|---|---|
| WO | 98/32326 | 7/1998 | ............ | A01H/4/00 |
| WO | 98/54961 | 12/1998 | | |
| WO | 00/58484 | 10/2000 | ........... | C12N/15/82 |

OTHER PUBLICATIONS

Hansen et. al. Trends in Plant Science, vol 4, pp. 226–231, 1999,.*
Bowen, Markers forn Plant Gene Transfer, pp. 89–123, in Transgenic Plants, vol. 1, 1993, Academic Press,.*
Bidney, D., et al., "Microprojectile bombardment of plant tissues increases transformation frequency by *Agrobacterium tumefaciens*", *Plant Molecular Biology*, 18, pp. 301–313, (1992).
Bolton, G.W., et al., "Plant Phenolic Compounds Induce Expression of the *Agrobacterium tumefaciens*Loci Needed for Virulence", *Science*, 232, pp. 983–985, (May 23, 1986).

Byrne, M.C., et al., "Strain and cultivar specificity in the Agrobacterium–soybean interaction", *Plant Cell, Tissue and Organ Culture, 8*, pp. 3–15, (1987).
Chee, P.P., et al., "Transformation of Soybean (Glycine max) by Infecting Germinating Seeds with *Agrobacterium tumefaciens*", *Plant Physiol., 91*, pp. 1212–1218, (1989).
Cho, H., et al., "High–efficiency induction of soybean hairy roots and propagation of the soybean cyst nematode", *Planta, 210 (2)*, pp. 195–204, (Jan. 2000).
Christou, P., et al., "Inheritance and Expression of Foreign Genes in Transgenic Soybean Plants", *Proc. Natl. Acad. Sci. USA, 86*, 7500–7504, (Oct. 1989).
Christou, P., et al., "Soybean genetic engineering—commercial production of transgenic plants", *Trends in Biotechnology, 8*, pp. 145–151, (Jun. 1990).
Christou, P., et al., "Stable transformation of soybean by electroporation and root formation from transformed callus", *PNAS, 84*, pp. 3962–3966, (Jun. 1987).
Clemente, T.E., et al., "Progeny Analysis of Glyphosate Selected Transgenic Soybeans Derived from Agrobacterium—Mediated Transformation", *Crop Science, 40*, pp. 797–803, (May/Jun. 2000).
Delzer, B.W., et al., "*Agrobacterium tumefaciens* Susceptibility and Plant Regeneration of 10 Soybean Genotypes in Maturity Groups 00 to II", *Crop Science, 30*, pp. 320–322, (1990).
Di, R., et al., "Production of transgenic soybean lines expressing the bean pod mottle virus coat protein precursor gene", *Plant Cell Reports, 15*, pp. 746–750, (1996).
Dye, F., et al., "Alkylsyringamides, new inducers of *Agrobacterium tumefaciens* virulence genes", *Biochimie, 1 (79)*, pp. 3–6, (1997).
Enriquez–Obregon, G.A., et al., "Agrobacterium–mediated Japonica rice transformation: a procedure assisted by an antinecrotic treatment", *Plant Cell, Tissue and Organ Culuture, 59 (3)*, pp. 159–168, (1999).
Finer, J.J., et al., "Transformation of Soybean Via Particle Bombardment of Embryogenic Suspension Culture Tissue", *In Vitro Cell. Dev. Biol., 27P*, pp. 175–182, (Oct. 1991).
Gamborg, O.L., "Plant Cell Cultures: Nutrition and Media", *Cell Culture ANS Somatic Cell Genetics of Plants*, pp. 18–26, (1984).

(List continued on next page.)

*Primary Examiner*—Elizabeth F. McElwain
*Assistant Examiner*—Georgia L. Helmer
(74) *Attorney, Agent, or Firm*—Schwegman, Lundberg, Woessner & Kluth, P.A.

(57) ABSTRACT

The invention provides a method to enhance Agrobacterium-mediated transformation of plant cells, parts and tissues, thereby enhancing the production of transgenic plants.

17 Claims, 25 Drawing Sheets

OTHER PUBLICATIONS

Hansen, G., et al., "Constitutive expression of the virulence genes improves the efficiency of plant transformation by Agrobacterium", *PNAS, 91*, pp. 7603–7607, (Aug. 1994).

Hinchee, M.A., et al., "Production of Transgenic Soybean Plants Using Agrobacterium–Mediated DNA Transfer", *Bio/Technology, 6*, pp. 915–922, (Aug. 1988).

Hsia, L.C., et al., "Nutrient Requirement of Growing—Finishing Pigs When Ad Libitum Under Hot and Cool Seasons III. The Effect of Energy Level of Food on the Carcass of Finishing Pigs", *J. Agric. Assoc. China, 40*, pp. 77–78, (1991).

Kartha, K.K., et al., "Plant regeneration from meristems of grain legumes: soybean, cowpea, peanut, chickpea, and bean", *Canadian Journal of Botany, 59(9)*, pp. 1671–1679, (Sep. 1981).

Komatsuda, T., et al., "Cell Biology & Molecular Genetics—Genotype X Sucrose Interactions for Somatic Embryogenesis in Soybean", *Crop Science, 31 (2)*, pp. 333–337, (1991).

Lin, W., et al., "Soybean Protoplast Culture and Direct Gene Uptake and Expression by Cultured Soybean Protoplasts", *Plant Physiol., 84*, pp. 856–861, (1987).

Liu, J., et al., "Effects of Butyrate Homologues on Metallothionein Induction In Rat Primary Hepatocyte Cultures", In Vitro *Cell. Dev. Biol., 28A*, pp. 320–326, (May 1992).

McCabe, D.E., et al., "Stable Transformation of Soybean (Glycine max) by Particle Acceleration", *Bio/Technology, 6*, 923–926, (Aug. 1988).

Meurer, C.A., et al., "Factors affecting soybean cotyledonary node transformation", *Plant Cell Reports, 18*, pp. 180–186, (1998).

Moore, P.J., et al., "Genotype and developmental regulation of transient expression of a reporter gene in soybean zygotic cotyledons", *Plant Cell Reports, 13*, pp. 556–560, (1994).

Parrott, W.A., et al., "Recovery and Evaluation of Soybean Plants Transgenic for a *Bacillus Thuringiensis* Var. Kurstaki Insecticidal Gene", In Vitro *Cell. Dev. Biol., 30P*, pp. 144–149. (Jul. 1994).

Parrott, W.A., et al., "Recovery of primary transformants of soybean", *Plant Cell Reports, 7*, pp. 615–617, (1989).

Perl, A., et al., "Establishment of an Agrobacterium–mediated transformation system for trape (*Vitis vinifera L.*): The role of antioxidants during grape–Agrobacterium interactions", *Nature Biotechnology, 14 (5)*, pp. 624–628, (May 1996).

Powell, W., et al., "In vitro genetics of barely (*Hordeum vulgare L.*): Response of immature embryos to a 2,4–dichlorophenoxyacetic acid", *Heredity, 58*, pp. 75–80, (1987).

Santarem, E.R., et al., "Sonication–assisted Agrobacterium––mediated transformation of soybean immature cotyledons: optimization of transient expression", *Plant Cell Reports, 17*, pp. 752–759, (1998).

Sato, S., et al., "Stable transformation via particle bombardment in two different soybean regeneration systems", *Plant Cell Reports, 12*, pp. 408–413, (1993).

Torisky, R.S., et al., "Development of a binary vector system for plant transformation based on the supervirulent *Agrobacterium tumefaciens* strain Chry5", *Plant Cell Reports, 17*, pp. 102–108, (1997).

Trick, H.N., et al., "Recent advances in soybean transformation", *Plant Tissue Culture and Biotechnology, 3 (1)*, pp. 9–26, (Mar. 1997).

Zambryski, P., et al., "Transfer and Function of T–DNA Genes from Agrobacterium Ti and Ri Plasmids in Plants", *Cell, 56*, pp. 193–201, (Jan. 27, 1989).

Zhang, Z., et al., "The use of glufosinate as a selective agent in Agrobacterium–mediated transformation of soybean", *Plant Cell, Tissue and Organ Culture, 56*, pp. 37–46, (1999).

McKently, A.H., et al., "Agrobacterium–mediated transformation of peanut (*Arachis hypogaea L.*) embryo axes and the development of transgenic plants", *Plant Cell Reports, 14 (11)*, pp. 699–703, (1995).

* cited by examiner

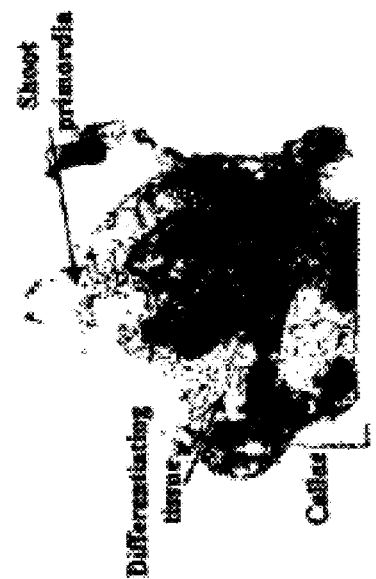
FIG. 1A2
FIG. 1A3
FIG. 1A1

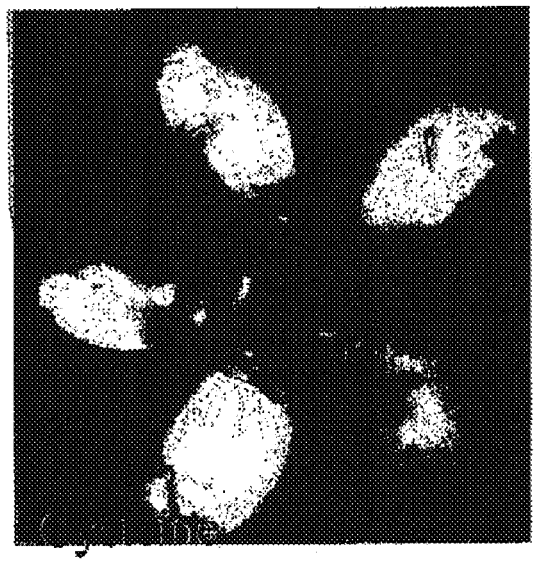 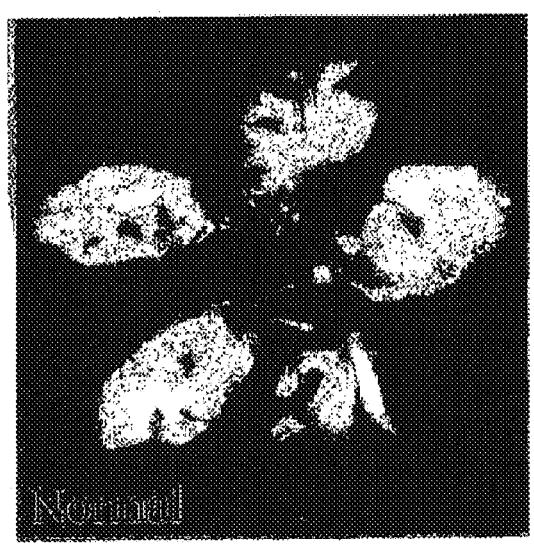
FIG. 1B1	FIG. 1B2

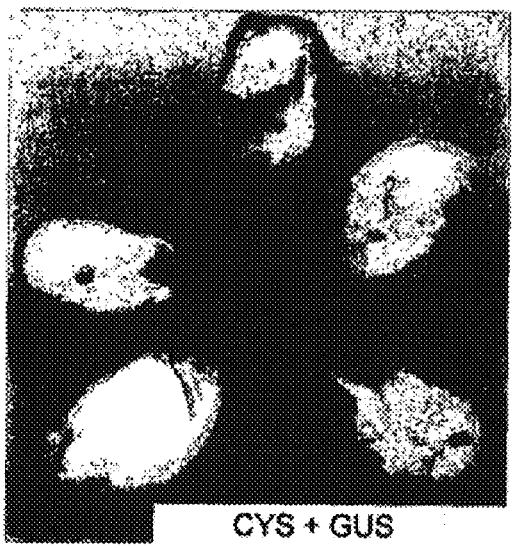
CYS + GUS
FIG. 1B3
0 mg/l CYS + GUS
FIG. 1B4

| Agrobacteria infection of soybean explants 5 days after co-culture | | | | | | | | |
|---|---|---|---|---|---|---|---|---|
| Exp. #1 | Genotype | Agrobact | Temps °C | None | very low | low | medium | good | superior |
| Cysteine 0 | Bert | AGL1 | 25 | x | x | | | | |
| Cysteine 100 | Bert | AGL1 | 25 | | | | | x | x |
| Cysteine 200 | Bert | AGL1 | 25 | | | | x | x | |
| Cysteine 300 | Bert | AGL1 | 25 | | | | | x | x |
| Cysteine 400 | Bert | AGL1 | 25 | | | | | | x |
| Exp. #2 | Genotype | Agrobact | Temps °C | None | very low | low | medium | good | superior |
| Cysteine 0 | MN1301 | AGL1 | 21 | | x | | | | |
| Cysteine 0 | MN1301 | AGL1 | 25 | | x | | | | |
| Cysteine 100 | MN1301 | AGL1 | 21 | | | | x | x | |
| Cysteine 100 | MN1301 | AGL1 | 25 | | | | x | x | |
| Cysteine 200 | MN1301 | AGL1 | 21 | | x | | | | |
| Cysteine 200 | MN1301 | AGL1 | 25 | | | | | x | |
| Cysteine 300 | MN1301 | AGL1 | 21 | | | | | x | x |
| Cysteine 300 | MN1301 | AGL1 | 25 | | | | x | x | |
| Cysteine 400 | MN1301 | AGL1 | 21 | | | | x | x | |
| Cysteine 400 | MN1301 | AGL1 | 25 | | | | x | x | |
| Exp. #3 | Genotype | Agrobact | Temps °C | None | very low | low | medium | good | superior |
| Cysteine 0 | MN0901 | AGL1 | 4/22 | | x | | | | |
| Cysteine 0 | MN0901 | AGL1 | 4/25 | x | x | | | | |
| Cysteine 0 | MN0901 | AGL1 | 28/22 | | | x | x | | |
| Cysteine 0 | MN0901 | AGL1 | 28/25 | | | x | | | |
| Cysteine 100 | MN0901 | AGL1 | 4/22 | | | x | | | |
| Cysteine 100 | MN0901 | AGL1 | 4/25 | | | | x | | |
| Cysteine 100 | MN0901 | AGL1 | 28/22 | | | | x | x | |
| Cysteine 100 | MN0901 | AGL1 | 28/25 | | | | x | x | |
| Cysteine 200 | MN0901 | AGL1 | 4/22 | | | x | x | | |
| Cysteine 200 | MN0901 | AGL1 | 4/25 | | | | | x | |
| Cysteine 200 | MN0901 | AGL1 | 28/22 | | | x | x | | |
| Cysteine 200 | MN0901 | AGL1 | 28/25 | | | | x | | |
| Cysteine 300 | MN0901 | AGL1 | 4/22 | | | | | x | |
| Cysteine 300 | MN0901 | AGL1 | 4/25 | | | | x | x | |

FIG. 1C

| | Genotype | Agrobact | Temps °C | None | very low | low | medium | good | superior |
|---|---|---|---|---|---|---|---|---|---|
| Cysteine 300 | MN0901 | AGL1 | 28/22 | | | | | x | x |
| Cysteine 300 | MN0901 | AGL1 | 28/25 | | | | | x | |
| Cysteine 400 | MN0901 | AGL1 | 4/22 | | | | | x | x |
| Cysteine 400 | MN0901 | AGL1 | 4/25 | | | | | x | x |
| Cysteine 400 | MN0901 | AGL1 | 28/22 | | | | | | x |
| Cysteine 400 | MN0901 | AGL1 | 28/25 | | | | | | x |
| Exp. #4 | Genotype | Agrobact | Temps °C | None | very low | low | medium | good | superior |
| Cysteine 0L0S | Bert | AGL1 | 28 | | | x | | | |
| Cysteine 0L0S | Bert | AGL1 | 4 | | x | | | | |
| Cysteine 400L0S | Bert | AGL1 | 28 | | x | | | | |
| Cysteine 400L0S | Bert | AGL1 | 4 | | x | | | | |
| Cysteine 0L400S | Bert | AGL1 | 28 | | | | | x | |
| Cysteine 0L400S | Bert | AGL1 | 4 | | | | x | | |
| Cysteine 400L400S | Bert | AGL1 | 28 | | | | | x | x |
| Cysteine 400L400S | Bert | AGL1 | 4 | | | | | x | x |
| Exp. #5 | Genotype | Agrobact | Temps °C | None | very low | low | medium | good | superior |
| Cysteine 0L0S | MN0901 | AGL1 | 25 | | | x | | | |
| Cysteine 400L0S | MN0901 | AGL1 | 25 | | | x | | | |
| Cysteine 0L400S | MN0901 | AGL1 | 25 | | | | | | x |
| Cysteine 400L400S | MN0901 | AGL1 | 25 | | | | | | x |
| Cysteine 400L400S | MN0901 | AGL1 | 21 | | | | | | x |
| | | | | | | | | | |
| Cysteine 0L0S | Granite | AGL1 | 25 | | x | | | | |
| Cysteine 400L0S | Granite | AGL1 | 25 | | x | | | | |
| Cysteine 0L400S | Granite | AGL1 | 25 | | | | x | | |

FIG. 1D

| | | | | None | very low | low | medium | good | superior |
|---|---|---|---|---|---|---|---|---|---|
| Cysteine 400L400S | Granite | AGL1 | 25 | | | | x | x | |
| | | | | | | | | | |
| Cysteine 0L0S | MN1401 | AGL1 | 25 | | x | | | | |
| Cysteine 400L0S | MN1401 | AGL1 | 25 | | x | | | | |
| Cysteine 0L400S | MN1401 | AGL1 | 25 | | | | x | | |
| Cysteine 400L400S | MN1401 | AGL1 | 25 | | | | x | | |
| Exp. #6 | Genotype | Agrobact | Temps °C | None | very low | low | medium | good | superior |
| Cysteine 0L0S | MN1301 | AGL1 | 25 | | x | | | | |
| Cysteine 400L0S | MN1301 | AGL1 | 25 | | x | | | | |
| Cysteine 0L400S | MN1301 | AGL1 | 25 | | | | | x | |
| Cysteine 400L400S | MN1301 | AGL1 | 25 | | | | | x | |
| Exp. #7 | Genotype | Agrobact | Temps °C | None | very low | low | medium | good | superior |
| Cysteine 0L0S | Bert | AGL1 | 25 | | x | | | | |
| Cysteine 0L400S | Bert | AGL1 | 25 | | | | | x | x |
| Cysteine 0L600S | Bert | AGL1 | 25 | | | | | x | x |
| Cysteine 0L800S | Bert | AGL1 | 25 | | | | | x | |
| Cysteine 0L1000S | Bert | AGL1 | 25 | | | | | x | |
| Exp. #8 | Genotype | Agrobact | Temps °C | None | very low | low | medium | good | superior |
| Cysteine 400L400S | MN0901 | NONE | 25 | x | | | | | |
| | | | | | | | | | |
| Cysteine 400L0S | MN0901 | LBA4404 | 25 | | x | x | | | |
| Cysteine 400L400S | MN0901 | LBA4404 | 25 | | | | | | xx |

FIG. 1E

| | Genotype | Agrobact | Temps °C | None | very low | low | medium | good | superior |
|---|---|---|---|---|---|---|---|---|---|
| Cysteine 400L0S | MN0901 | AGL1 | 25 | | x | | | | |
| Cysteine 400L400S | MN0901 | AGL1 | 25 | | | | | x | |
| | | | | | | | | | |
| Cysteine 400L0S | MN1801 | AGL1 | 25 | | x | | | | |
| Cysteine 400L400S | MN1801 | AGL1 | 25 | | | | x | x | |
| | | | | | | | | | |
| Cysteine 400L0S | MN0301 | AGL1 | 25 | | x | | | | |
| Cysteine 400L400S | MN0301 | AGL1 | 25 | | | | x | | |
| | | | | | | | | | |
| Cysteine 400L0S | Lambert | AGL1 | 25 | | x | | | | |
| Cysteine 400L400S | Lambert | AGL1 | 25 | | | | x | x | |
| Exp. #9 | Genotype | Agrobact | Temps °C | None | very low | low | medium | good | superior |
| Methionine | MN0901 | LBA4404 | 25 | | x | | | | |
| Methionine | MN0901 | LBA4404 | 22 | | | x | | | |
| Methionine | MN0901 | AGL1 | 25 | | x | | | | |
| Methionine | MN0901 | AGL1 | 22 | | x | | | | |
| | | | | | | | | | |
| Glutathione | MN0901 | LBA4404 | 25 | x | | | | | |
| Glutathione | MN0901 | LBA4404 | 22 | | x | | | | |
| Glutathione | MN0901 | LBA4404 | 25 | x | | | | | |
| Glutathione | MN0901 | LBA4404 | 22 | | x | | | | |
| | | | | | | | | | |
| Cysteine 400 | MN0901 | LBA4404 | 22 | | | | | | x |
| Cysteine 400 | MN0901 | LBA4404 | 25 | | | | | | x |
| Cysteine 400 | MN0901 | AGL1 | 22 | | | | | x | |
| Cysteine 400 | MN0901 | AGL1 | 25 | | | | | x | |
| Cysteine 0 | MN0901 | LBA4404 | 22 | | | x | | | |
| Cysteine 0 | MN0901 | LBA4404 | 25 | | | x | | | |

FIG. 1F

| Cysteine 0 | MN0901 | AGL1 | 22 | | x | | | | |
|---|---|---|---|---|---|---|---|---|---|
| Cysteine 0 | MN0901 | AGL1 | 25 | | x | | | | |
| | | | | | | | | | |
| Cysteine 0 | Lambert | AGL1 | 22 | | x | | | | |
| Cysteine 0 | Lambert | AGL1 | 25 | | x | | | | |
| Cysteine 400 | Lambert | AGL1 | 22 | | | | | | |
| Cysteine 400 | Lambert | AGL1 | 25 | | | x | | | |

FIG. 1G

| Bert | Cysteine Experiment #1 | | | | | |
|---|---|---|---|---|---|---|
| | | | | | % Explants with shoots | $\bar{x}$ |
| 0 mg Cysteine | 3 | 0 | 0 | 6 | 0% | 2.9 |
| | 0 | 1 | 0 | 10 | | |
| | 8 | 2 | 6 | 2 | | |
| | 4 | 0 | 2 | | | |
| 50 mg Cysteine | 6 | 8 | 4 | 2 | 6.25% | 4.0 |
| | 7 + 2 shoots/events | 2 | 5 | 10 | | |
| | 0 | 9 | 2 | 1 | | |
| | 3 | 6 | 0 | 0 | | |
| 100 mg Cysteine | 8 + 1 shoot | 5 + 4 shoots | 2 | 0 | 20% | 4.3 |
| | 2 | 9 + 1 shoot | 4 | 5 | | |
| | 6 | 4 | 4 | 7 | | |
| | 3 | 5 | 1 | | | |
| 150 mg Cysteine | 14 | 3 | 2 | 15 | 14.3 | 6.5 |
| | 8 | 9 | 4 | 12 + 1 shoot | | |
| | 11 | 2 | 3 | | | |
| | 3 | 7 | 8 + 2 shoots | | | |
| 200 mg Cysteine | 14 | 9 | >18 + 4 shoots | 10 | 18.7 | 14.9 |
| | 12 | >23 | 11 | 17 | | |
| | 15 + >5 cluster | 17 | >30 | 19 + 1 shoot | | |
| | 10 | 6 | 12 | 16 | | |

FIG. 2

| MN1301 | Cysteine Experiment #1 | | | | | |
|---|---|---|---|---|---|---|
| | | | | | % Explants with shoots | x̄ |
| 0 mg Cysteine | 0 | 2 | 0 | | 0% | 1.9 |
| | 1 | 7 | | | | |
| | 3 | 0 | | | | |
| | 3 | 1 | | | | |
| 50 mg Cysteine | 5 | 5 | | | 0% | 9.4 |
| | 7 | 6 | | | | |
| | 12 | 13 | | | | |
| | 15 | 12 | | | | |
| 100 mg Cysteine | 14 | 17 + 1 shoot | 26 | | 9% | 15.6 |
| | 12 | >23 | 29 | | | |
| | 16 | 5 | 18 | | | |
| | 12 | 0 | | | | |
| 150 mg Cysteine | 1 | 15 | 26 | 17 | 0% | 11.8 |
| | 8 | 17 | 23 | 3 | | |
| | 19 | 4 | 18 | 5 | | |
| | 5 | 1 | 20 | 7 | | |
| 200 mg Cysteine | 16 | 8 | 16 | | 0% | 18.2 |
| | 27 | >20 | 4 | | | |
| | 23 | 25 | | | | |
| | 28 | >15 | | | | |

FIG. 3

MN0901                    Cysteine Experiment #1

| | 4°C pre-treatment | | No pre-treatment | | % | $\bar{\bar{x}}$ |
|---|---|---|---|---|---|---|
| | 22°C incubation | 25°C incubation | 22°C incubation | 25°C incubation | | |
| 0 mg Cysteine | 4<br>1<br>5<br>18    $\bar{x}=7$ | 0<br>7<br>8 + 1 shoot<br>1    $\bar{x}=4$ | 9<br>5<br>2<br>8    $\bar{x}=6$ | 6<br>6<br>1<br>12    $\bar{x}=6.2$ | 6.25% | 5.9 |
| 50 mg Cysteine | 13<br>8<br>14<br>4    $\bar{x}=4.7$ | 3<br>11<br>8<br>7    $\bar{x}=7.2$ | 14<br>11<br>12<br>17    $\bar{x}=13.5$ | 6<br>4<br>9<br>7    $\bar{x}=6.5$ | 0% | 4.2 |
| 100 mg Cysteine | 5<br>1<br>16<br>7    $\bar{x}=7.2$ | 2<br>4<br>5<br>2    $\bar{x}=3.2$ | 0<br>11<br>16<br>18 + 1 shoot<br>$\bar{x}=11.2$ | 13<br>19<br>19<br>7    $\bar{x}=14.5$ | 6.25% | 9.0 |
| 150 mg Cysteine | 12<br>14<br>9<br>12    $\bar{x}=11.7$ | 9<br>19<br>22<br>15    $\bar{x}=16.2$ | >16 +<br>>15 shoots<br>11 + 1 shoot<br>6<br>16    $\bar{x}=12.2$ | 16 + >5 shoots<br>24<br>20<br>12    $\bar{x}=19$ | 18.7% | 14.7 |
| 200 mg Cysteine | 19<br>14<br>10<br>9    $\bar{x}=13$ | 9<br>14<br>12<br>14    $\bar{x}=12.2$ | 24<br>12<br>16<br>16    $\bar{x}=17$ | 13<br>14<br>25<br>6    $\bar{x}=14.5$ | 0% | 14.1 |

FIG. 4

Bert Cysteine Experiment #2

| Bert | 0 mg Cysteine Liquid Co-culture media | | 200 mg Cysteine Liquid Co-culture media | | % | $\bar{\bar{x}}$ |
|---|---|---|---|---|---|---|
| | 5 mg/L ppt | 3.33 mg/L ppt | 5 mg/L ppt | 3.33 mg/L ppt | | |
| 0 mg Cysteine Solid Media | 4<br>1<br>0<br>2 + 2 shoots<br>4<br>0    $\bar{x} = 1.8$ | 2<br>3<br>4<br>4<br>5<br>2    $\bar{x} = 3.3$ | 2<br>1<br>3<br>1<br>4<br>3    $\bar{x} = 2.3$ | 7<br>1<br>3<br>0<br>3<br>3    $\bar{x} = 2.8$ | 4.2% | 2.5 |
| 200 mg Cysteine Solid Media | 9<br>14 + 8 shoots MASS<br>11<br>>24 + 5 shoots<br>35 + 1 shoot<br>7    $\bar{x} = 20.1$ | 5<br>>25<br>>27 + 1 shoot<br>27<br>11<br>>18    $\bar{x} = 18.8$ | 3<br>8 + 2 shoots<br>4<br>17<br>20<br>>15    $\bar{x} = 11.1$ | 12<br>7<br>11<br>8<br>19 + 1 shoot<br>6    $\bar{x} = 10.5$ | 25% | 15.1 |

FIG. 5

| CYSTEINE mg/l | # EXPLANTS WITH SHOOT PRIMORDIA/ TOTAL EXPLANTS | |
|---|---|---|
| 0 | 4/88 | 4.6 |
| 50 | 0/4 | ∅ |
| 100 | 1/16 | 6.3 |
| 200 | 3/15 | 20 |
| 300 | 2/23 | 9% |
| 400 | 17/105 | 16% |
| 600 | 5/10 | |
| 800 | 1/22 | 4% |
| 1000 | 7/34 | 20 |
| 1500 | 1/8 | |
| 2000 | 1/3 | |

| Bert | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 190 | 10 | 0 | 100/180 = 55.5% | 180 | | |
| 400 mg/l Cysteine | 190 | 10 | 0 | 160/180 = 88.8% | 180 | 705, 641 | 705, 641 |

* Includes those explants with zero shoot growth

| A3237 | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 188 | 10 | 0 | 118/178 = 66.3% | 178 | 644 | 644 |
| 400 mg/l Cysteine | 188 | 10 | 0 | 151/178 = 84.8% | 178 | 657, 655, 643 | 657, 655, 643 |

* Includes those explants with zero shoot growth

| Bert | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 205 | 10 | 0 | 143/195 = 73% | 195 | | |
| 1000 mg/l Cysteine | 210 | 10 | 0 | 160/200 = 80% | 200 | 525, 527, 666, 627, 620, 611, 590, 564, 661 | 525, 527, 666, 627 |

* Includes those explants with zero shoot growth

FIG. 13A

| A3237 | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 190 | 10 | 75 | NA contamin. | 105 | | |
| 1000 mg/l Cysteine | 195 | 10 | 56 | NA contamin. | 129 | 630 | 630 |

*Includes those explants with zero shoot growth
**Many more explants tossed throughout experiment, any % efficiency will be underestimated.

| Hygro #1 | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 213 | 7 | 4 | 164/202 = 81.2% | 202 | | |
| 400 mg/l Cysteine | 213 | 7 | 2 | 182/204 = 89.2% | 204 | 694, 695 | 694, 695 |

*Includes those explants with zero shoot growth

| Hygro #2 | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 219 | 7 | 39 | 1145/173 = 83.8% | 173 | | |
| 400 mg/l Cysteine | 220 | 7 | 17 | 179/196 = 91.3% | 196 | | |

*Includes those explants with zero shoot growth

FIG. 13B

| Hygro #3 Bert | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 100 | 7 | 5 | 77/88 = 87.5% | 88 | | |
| 400 Cys | 107 | 7 | 0 | 88/100 = 88% | 100 | | |
| 1 mM DTT | 105 | 7 | 2 | 75/96 = 78% | 96 | 703 | 703 |
| 400 Cys + 1 mM DTT | 100 | 7 | 6 | 77/87 = 88.5% | 87 | | |
| 400 Cys + 0.3 mM DTT | 25 | 7 | 0 | 17/18 = 94.4% | 18 | | |

* Includes those explants with zero shoot growth

| Hygro #4 Bert | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 116 | 7 | 38 | 67/71 = 94.4% | 71 | | |
| 400 Cys | 116 | 7 | 38 | 67/71 = 94.4% | 71 | | |
| 1 mM DTT | 116 | 7 | 11 | 79/98 = 80.6% | 98 | | |
| 400 Cys + 1 mM DTT | 116 | 7 | 29 | 73/80 = 91.25% | 80 | 696, 699 | 696, 699 |

* Includes those explants with zero shoot growth

FIG. 13C

| Hygro #5 Bert | # Explants Inoculated | # Explants Sacrificed | # Explants Contaminated | % Shoot Formation | Total # Explants* | Elongated Shoots | Independent Events |
|---|---|---|---|---|---|---|---|
| 0 control | 110 | 7 | 1 | 81/102 = 79.1% | 102 | | |
| 1000 Cys | 110 | 7 | 1 | 91/102 = 89.2% | 102 | | |
| 1 mM DTT | 110 | 7 | 3 | 77/100 = 77% | 100 | | |
| 1000 Cys + 1 mM DTT | 113 | 7 | 16 | 88/104 = 84.6% | 104 | | |

* Includes those explants with zero shoot growth

FIG. 13D

METHOD TO ENHANCE AGROBACTERIUM-MEDIATED TRANSFORMATION OF PLANTS

CROSS REFERENCE TO RELATED APPLICATIONS

The present application claims the benefit of the filing date of U.S. application Ser. No. 60/170,981, filed Dec. 15, 1999, and U.S. application Ser. No. 60/224,715, filed Aug. 11, 2000, the disclosures of which are incorporated by reference herein.

BACKGROUND OF THE INVENTION

Soybean [*Glycine max* (L.) Merr.] is one of the world's most important agronomic crops. Between 120 and 130 million acres are planted annually, resulting in 105 million tons of seed. Soybeans have dominated world oilseed production among the eight major oilseeds traded in international markets, accounting for over 97% of all world oilseed production since 1965. The value of the crop is estimated to be over 20 billion dollars. Both soybean oil and protein are used extensively in food products for human consumption. In the United States, 5% of the total protein is derived from grain legumes and up to 65% of the oil used by the food processing industry comes from soybean (Hoskin, 1987; Smith and Huyser, 1987).

Although a great deal of effort has been devoted towards the development of new cultivars of soybean with improved disease resistance, along with increased nutritional value, traditional breeding programs have been restricted because soybean germplasm is extremely narrow and the majority of the soybean cultivars in use are derived from very few parental lines (Christou et al., 1990).

Hence, modification of soybean using genetic engineering techniques would facilitate the development of new varieties with traits such as disease resistance, e.g., viral resistance, pest resistance, and herbicide resistance, and seed quality improvement in a manner unattainable by traditional breeding methods or tissue-culture induced variation. To attain genetically modified plants, a transformation system must be developed to optimize the integration of DNA in the plant, which is most commonly delivered using either an Agrobacterium-based system, which requires wounding of plant cells (Zambryski et al., 1989), or particle bombardment (Biolistics). Although transgenic soybean plants have been produced using both microprojectile bombardment (McCabe et al., 1988; Christou, P. et al., 1989) and various Agrobacterium-mediated transformation methods (Hinchee et al., 1988; Chee et al., 1989; Parrott et al., 1989; Clemente and Zhang, 2000; Di et al., 1996), legumes, including soybeans remain extremely recalcitrant to transformation (Trick, 1997). And while successes in producing transgenic plants have been reported, the frequency of attaining transgenic plants is low, e.g., Parrott et al. (1994) report 1 transgenic plant out of 195 regenerated, and Zhang et al. (1999) report that the efficiency of producing marker-positive plants in five independent attempts was 0%, 0%, 0.5%, 0.7% and 3.0%. The demand and need for new and useful transgenic soybeans is evident from the fact that transgenic soybeans, which were derived from a single transgene integration event, represent more than 50% of the total commercial production of soybeans grown in the United States. In addition, the recalcitrant nature of soybeans to transformation has rendered many molecular, genetic, and genomic techniques commonly used in other major crops, such as maize, impractical.

The "cot-node" method is a frequently used soybean transformation system based on Agrobacterium-mediated T-DNA delivery into regenerable cells in the cotyledonary node. For example, U.S. Pat. No. 5,322,783 relates to a method for transformation of soybean tissue in which cotyledonary node cells are treated with a cytokinin, and then the cells are bombarded with microparticles carrying specific vectors and exogenous DNA. U.S. Pat. Nos. 5,169,770 and 5,376,543 disclose a method in which soybean seeds are germinated, and the meristematic or mesocotyl cell tissues are inoculated with bacterial cells, specifically Agrobacterium strains which, through infection, transfer DNA into these explants.

In U.S. Pat. No. 4,992,375, a process is described in which the cotyledonary node region from a donor plant is excised, and the explant is cultured in a nutrient media containing cytokinin, until shoots arose from resultant callus. The shoots are then rooted. U.S. Pat. No. 5,416,011 also utilizes a cotyledon explant, which requires removal of the hypocotyl, saving and separating the cotyledons, and inserting a chimeric gene by inoculation with *Agrobacterium tumefaciens* vectors containing the desired gene. The histochemical marker GUS was employed to determine successful transformation. Nevertheless, the efficiency of the cot-node transformation system remains low apparently because of poor Agrobacterium infection of cot-node cells, inefficient selection of transgenic cells that give rise to shoot meristems, and low rates of transgenic shoot regeneration and plant establishment.

A number of reports on soybean regeneration utilized cotyledons from immature zygotic embryos induced to undergo somatic embryogenesis (Liu et al., 1992). Soybean regeneration through short meristem cultures resulted in up to 35% explants responding to plant regeneration 4 weeks after culture (Kartha et al., 1981). Regeneration via organogenesis utilizing different explants has been reported with a maximum of 97% of explants responding and 3 shoots produced per explant 10 weeks after culture, and 38% of shoots developing roots for another 4 weeks (Yeh et al., 1991). However, interactions between genotype and in vitro cultural conditions (medium, explant and light treatment) have not been reported in regeneration via organogenesis or meristem culture in soybean, although it has been studied in regeneration via somatic embryogenesis and was proven important (Powell et al., 1987; Komatsuda et al., 1991).

The unreliable transformation and regeneration of legumes in general is due, in part, to the difficulty in producing fertile mature plants from tissue culture as well as legumes being extremely resistant to Agrobacterium infection. Thus, although genes have been transferred to soybean protoplasts by electroporation of free DNA (Christou et al., 1987; Lin et al., 1987), regeneration technology for soybean has not progressed to a state where regenerated plants can be produced from protoplasts. For example, the formation of shoots, and eventual rooting, takes place only in a tiny fraction of the cases. Further, successful transformation and successful regeneration are frequently cultivar-specific, with no broad success. See, for example, Wayne et al., 1988; Finer et al., 1991; Sato et al., 1993; Moore et al., 1994; Parrott et al., 1994 and Steart et al., 1996.

Improvements have been reported in the three components of the cot-node transformation system. For example, improved selection systems and plant regeneration have been developed (Zhang et al., 1999). Considerable effort also has been applied to increasing Agrobacterium virulence by addition of chemical inducers of the vir genes (Bolton et al., 1986; Dyé et al., 1997), improvements in vir gene constructs (Hansen et al., 1994; Torisky, 1997), identification and selection of susceptible soybean cultivars (Meuer et al., 1998; Byrne et al., 1987; Delzer et al., 1990; Cho et al., 2000), and increasing the wounding of explants by either microprojectile bombardment or sonication (Bidney et al., 1992; Santarem et al., 1998).

Although agents such as dithiothreitol (DTT) and polyvinylpolypyrrolidone (PVPP) increase plant viability after Agrobacterium-mediated transformation of grape (Perl et al., 1996) and ascorbic acid, the amino acid, cysteine, and silver nitrate individually or in combination decreased damage and increased viability of Japonica rice meristem cultures and, in combination, decreased the Agrobacterium-mediated tissue necrosis of those cultures (Enríguez-Obregón et al., 1999), no agents have been reported to enhance the Agrobacterium-mediated transformation efficiency of soybeans.

Thus, what is needed is a method to reproducibly enhance the transformation of plants, e.g., soybeans.

SUMMARY OF THE INVENTION

The invention provides a method for transforming a plant cell, part or tissue. Preferred plant cells, parts or tissue for use in the method of the invention are those which can be regenerated to a plant. The method comprises contacting a plant cell, part or tissue, e.g., a cotyledon explant from a plant seedling, with a Agrobacterium, e.g., *A. tumefaciens* or *A. rhizogenes*, containing DNA to be introduced into the plant cell, part or tissue and at least one agent in an amount that enhances Agrobacterium-mediated transformation so as to yield a transformed plant cell, part or tissue. Then a transformed plant cell, part or tissue is identified. Preferably, the plant cell, part or tissue is wounded prior to contact. For example, for a cotyledonary explant, the cotyledon is wounded in the region of the axillary bud and/or cotyledonary node. The cotyledon may be prepared by (i) removing the hypocotyl region of a seedling by cutting in the region just below the cotyledonary node, for example, from about 0.2 to about 1.5 cm below the cotyledonary node; (ii) splitting and completely separating the remaining attached hypocotyl segment, also thereby separating the two cotyledons; and (iii) removing the epicotyl from the cotyledon, e.g., to which it remains attached. Prior to removing the hypocotyl region, the seedling may be incubated at about 0° C. to about 30° C., e.g., 0° C. to about 10° C. or 15° C. to about 30° C., for at least 24 hours. Preferably, the seedling is a 5-day germinated seedling that is bisected between the cotyledons along the embryonic axis. The epicotyl is excised and the cot-node cells are wounded with a scalpel by extensive cutting of the node at the base of the cotyledon. Then the wounded cotyledon is contacted with a Agrobacterium vector, e.g., a disarmed *A. tumefaciens* vector containing DNA, the cot-node explants are cultivated on solid medium for 5 days and transformed explant tissue is identified, e.g., by selection. Sources of the plant cell, plant part, or plant tissue include both dicots and monocots, including agricultural crops, ornamental fruits, vegetables, trees and flowers. In one embodiment, the plant cell, part or tissue is that of a legume. Preferably, a differentiated transformed plant is regenerated from the transformed plant cell, part or tissue.

Preferred agents for use in the methods of the invention include, but are not limited to, those which inhibit enzymatic browning of plant tissue, plant cells, or parts of a plant, in response to wounding, e.g., an agent that inhibits the activity or production of enzymes associated with browning such as polyphenol oxidase (PPO) and peroxidase (POD), chelators of metals required for activity of the enzymes associated with browning, as well as sulfhydryl-containing agents, e.g., cysteine, L-cystine, DTT, ascorbic acid, sodium thiosulfate, and glutathione.

As described hereinbelow, the Agrobacterium-mediated infection of soybean explants in the cot-node region was increased from 30% to 100% by employing an agent of the invention and the following general protocol. Under aseptic conditions, the axillary region near the node located between the cotyledon and hypocotyl of 5-day old soybean seedlings was excised. The explant tissued was dissected from the entire seedling by cutting the hypocotyl approximately 0.5 cm to 1 cm below the cotyledon and cutting lengthwise down the hypocotyl resulting in two separate explants. After the epicotyl was removed, the entire node region, including the axillary region, was wounded with a scalpel, and the explant was co-cultivated in a liquid Agrobacterium culture before placing the explant on a solid co-cultivation media for 5 days. For example, Agrobacterium strain AGL1 and a binary plasmid BSF16 that contains the bar gene for herbicide (PPT) selection, the β-glucoronidase (GUS) gene for a phenotypic marker, and a sulfur-rich gene, albumin, from sunflower driven by a seed-specific promoter, was employed. De novo shoot formation occurred at the site of the axillary meristem when grown in a shoot induction media under herbicide selection after four weeks. After this time, elongation of herbicide-resistant shoots was induced for up to ten weeks on a shoot elongation media.

Surprisingly, the addition of the sulfhydryl compound L-cysteine to the co-cultivation media during the 5-day incubation step increased the amount of GUS$^+$ sectors at the cot-node region dramatically. For example, Agrobacterium was suspended in the liquid co-culture for about 1 hour to about 2 hours and then the wounded explant was added to the Agrobacterium liquid co-culture for about one half of an hour. The explants were then placed on solid co-culture media for 5 days. The Minnesota genotypes Bert, MN1301, and MN0901 were employed with either 0 mg/l, 100 mg/l, 200 mg/l, 300 mg/l, or 400 mg/l L-cysteine. Transient assay experiments after the 5-day incubation period resulted in 80–100% infection (% of explants) at the entire cot-node region, the appearance of GUS$^+$ foci on the cotyledon, as well as extensive GUS$^+$ foci along the cut hypocotyl surface, in explants contacted with cysteine containing media. Similar results were observed with the strain LBA4404 containing the pTOK233 binary plasmid. Generally, in the absence of cysteine, only 50% of control explants showed infection in the cot-node region and at a much reduced frequency. It is also very rare to detect GUS$^+$ foci on the cotyledon tissue.

As further described hereinbelow, under a low selection pressure (1.6 to 3.33 mg/l PPT), the control (0 mg/l cysteine) on average had 3.3 GUS$^+$ foci/explant scored, while explants co-cultivated in 400 mg/l cysteine had an average of 15.6 GUS$^+$ foci/explant scored after 4 weeks of shoot initiation. Moreover, increasing selection pressure during shoot induction may also increase the number of GUS$^+$ shoots. Plants co-cultivated in 0 mg/l cysteine or 400 mg/l cysteine were placed in shoot induction media containing either 5 mg/l or 3.33 mg/l PPT. The results were as followed: 33.3% of explants had GUS$^+$ shoots in 400 mg/l cysteine and 5 mg/l PPT, 16.6% of explants had GUS$^+$ shoots in 400 mg/l cysteine and 3.33 mg/A PPT, 8.3% of explants had GUS$^+$ shoots in 0 mg/l cysteine and 5 mg/l PPT, 0% of explants had GUS$^+$ shoots in 0 mg/l cysteine 3.33 mg/l PPT. Thus, adding cysteine to the co-cultivation media increases the frequency of Agrobacterium infection in the cot-node region, and results in at least a 5-fold increase in stable T-DNA transfer in newly developed shoot primordia. Other sulfhydryl-containing agents and inhibitors of the production or activity of PPO and POD also increased the frequency of transformation of soybean explants. Thus, agents of the invention reproducibly resulted in an enhanced efficiency of Agrobacterium-mediated transformation and so enhance the efficiency of producing stably transformed plants, which is particularly useful for plant tissues or cells that are difficult to transform.

Cysteine (e.g., at 400–1000 mg/l) in the solid co-cultivation medium also decreased enzymatic browning of soybean and fava bean explants. As untreated explants exhibit enzymatic browning at the wound sites on the cot-node and the cut surfaces of the hypocotyls following co-cultivation, explant wounding and infection likely activate wound and pathogen defense responses that may limit Agrobacterium-mediated T-DNA delivery to cot-node cells. The soybean cotyledon is known to be extremely responsive to pathogen attack, as exemplified by the synthesis of phytoalexins upon exposure to fungal elicitors (Boue et al., 2000). Thus, agents which inhibit the wound and pathogen defense responses on wounded and Agrobacterium-infected cot-node explants result in a reduction in enzymatic browning and tissue necrosis, increased T-DNA delivery and increased stable integration of T-DNA into the cot-node region.

In eight independent experiments, the addition of cysteine (400–1000 mg/l) resulted in: (1) an increase in the frequency of explants with at least one GUS$^+$ focus at the cot-node from 30–100% five days post-inoculation, (2) an increase in the number of GUS$^+$ foci per explant five days post-inoculation, (3) a 3.6-fold increase in stable T-DNA integration after 28 days, (4) a 5-fold increase in GUS$^+$ shoot primordia after 28 days, and (5) a 2-fold increase in production of transgenic plants. Increases in T-DNA transfer also resulted from the addition of D-cysteine, cystine, glutathione, dithiothreitol, sodium thiosulfate, and two metal chelators, bathocuproine disulfonic acid and bathophenanthroline disulfonic acid, and thus ultimately increases transgenic plant production. Preferably, the agent results in an increased stable transformation efficiency, for example, at least an increase of 0.5 to 50%, more preferably at least an increase of 2% or more, e.g., 3%, 5%, 10%, 15%, 20% or more.

Also provided is a method for transforming a plant cell, part or tissue in which the plant cell, part or tissue, e.g., apical meristem, is contacted with DNA, e.g., using a particle gene gun, and at least one agent of the invention so as to yield a transformed plant cell, part or tissue. Then a transformed plant cell, part or tissue is identified. Preferably, the addition of the agent to the plant cell, part or tissue results in an increased transformation efficiency relative to a plant cell, part or tissue which is contacted with DNA but not with the agent.

The invention also provides a method for transforming legumes. The method comprises contacting a wounded cotyledon explant from a legume seedling with an Agrobacterium containing DNA to be introduced into the explant and at least one agent of the invention so as to yield transformed explant tissue. The cotyledon is wounded in the region of the axillary bud and/or cotyledonary node. Transformed explant tissue is then identified, e.g., using a phenotypic marker present on the DNA which is introduced to the explant and/or a selectable marker such as an herbicide resistance marker. Preferably, a differentiated transformed plant is regenerated from the transformed explant tissue.

Therefore, the invention includes methods of transforming plant cells or tissues, e.g., legumes such as soybean plants, as well as regeneration of transformed tissues. Either the transformation or regeneration protocols can be used separately, but together, they provide an effective method for obtaining transgenic plants, to answer the needs of commercial farming and manufacturing. Accordingly, while both the regeneration protocol, and the transformation protocol, are described separately, it should be understood that they can, and preferably are, used in combination.

The invention also provides a transformed or transgenic plant or transformed explant prepared by the methods of the invention. For example, the invention provides transformed soybean and soybean tissue prepared from a seedling cotyledon pair containing an epicotyl, axillary buds, and hypocotyl tissue, comprising a single cotyledon containing an axillary bud and associated hypocotyl segment extending from about 0.2 to about 1.5 cm below the cotyledonary node. The associated hypocotyl segment is completely separated from its adjacent hypocotyl segment attached to the remaining cotyledon, thus separating the cotyledons. The epicotyl has been removed from the cotyledon to which it is attached, and the cotyledon is wounded in the region of the axillary bud and/or cotyledonary node. The wounded cotyledon is then contacted with Agrobacterium in the presence of an agent, e.g., cysteine, which enhances Agrobacterium infection.

Also provided is a method to identify an agent that enhances the transformation of a plant cell, plant tissue or plant part by Agrobacterium. The method comprises contacting a plant cell, plant tissue or plant part with Agrobacterium containing DNA to be introduced into the explant and at least one agent so as to yield transformed explant tissue, wherein the plant cell, plant tissue or plant part is wounded. The agent is not a phenolic, e.g., acetosyringone. Then it is determined whether Agrobacterium-mediated transformation of the plant cell, part or tissue is enhanced in the presence of the agent relative to Agrobacterium-mediated transformation of a plant cell, part or tissue which is not contacted with the agent.

Also provided is a plant medium comprising an agent of the invention. For example, the invention includes aqueous, powdered or solid media for culturing, e.g., propagating, or regenerating plant tissue, e.g., apical meristems, plant cells or a plant, which media comprises at least one of the agents of the invention. The media may be employed for propagation, e.g., micropropagation, or regeneration, of untransformed or transformed plant parts, tissue or cells, including protoplasts, e.g., from sorghum or azaleas. Preferred media are those for horticultural or floracultural purposes. In one preferred embodiment of the invention, the media is employed for propagation of tissue or cells from epiphytes, e.g., bromeliads, such as orchids. In another embodiment, the medium is one other that that employed for epiphytes. In other preferred embodiments, the medium is employed to propagate protoplasts from any plant source. Preferred agents for use in the media compositions of the invention include, but are not limited to, chelators of metals required for activity of PPO and/or POD, inhibitors of the production or activity of PPO or POD, as well as sulfhydryl-containing agents, e.g., cysteine, ascorbic acid, L-cystine, sodium thiosulfate, glutathione, or any combination thereof. Preferred media compositions of the invention are non-liquid compositions, e.g., powder or crystal formulations, comprising at least one of the agents of the invention in an preferably in an amount effective to enhance plant cell, tissue or plant survivability, decrease browning of plant cells, plant tissue or plants, inhibit the production or activity of PPO or POD in the plant cells, plant tissue or plant, or any combination thereof.

BRIEF DESCRIPTION OF THE FIGURES

FIG. 2 shows the number of GUS$^+$ foci/sector on each individual Bert explant after 4 weeks. The number of explants with shoots is noted. Bold and italicized explant numbers indicate a sector in tissue that gave rise to shoots.

FIG. 3 shows the number of GUS$^+$ foci/sector on each individual MN1301 explant after 4 weeks. The number of explants with shoots is noted. Bold and italicized explant numbers indicate a sector in tissue that gave rise to shoots.

FIG. 4 shows the number of GUS$^+$ foci/sector on each individual MN0901 explant after 4 weeks. The number of explants with shoots is noted. Bold and italicized explant numbers indicate a sector in tissue that gave rise to shoots.

FIG. 5 depicts the number of GUS$^+$ foci/sector on Bert explants in the presence of various concentrations of L-cysteine and PPT.

FIG. 13 illustrates the results obtained using ppt or hyg as the selection marker in the presence or absence of an agent of the invention.

DETAILED DESCRIPTION OF THE INVENTION

Figure 1H:
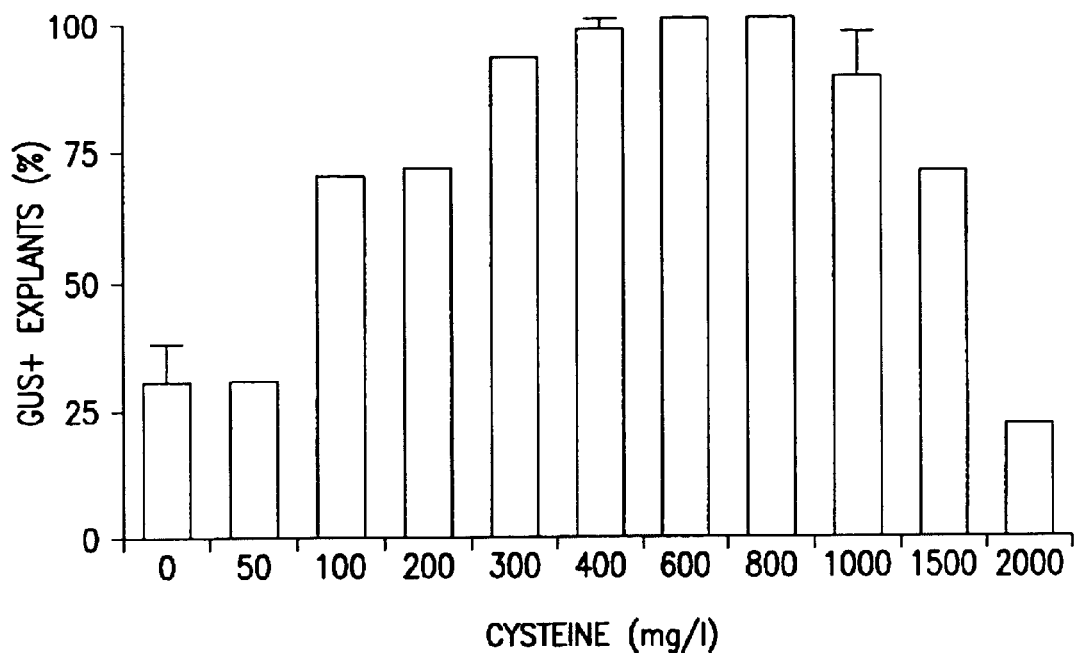
FIGS. 1A–D depict levels of Agrobacterium-mediated infection of soybean explants 5 after co-culture or 28 days in shoot induction media. A) (1) shows an explant at 5 days after co-culture with at least one GUS$^+$ foci at the cot-node region. A) (2) shows a sliced explant after 28 days in shoot induction media with GUS staining, and A) (3) shows stable T-DNA integration. B) shows enzymatic browning on treated and untreated explants with (bottom) and without (top) GUS staining. C) is data from experiments with cysteine concentrations ranging from 0–400 mg/l. D) depicts the average frequency of explants exhibiting at least one GUS$^+$ focus in the cot-node region across eight experiments. Standard error between experiments is represented by [⊥] above each cysteine treatment (0 mg/l r=8, n=106; 400 mg/l r=6, n=79, 1000 mg/l r=5, n=41). Both treatments of 400 and 1000 mg/l cysteine significantly differ from 0 mg/l cysteine at α=0.05 (P<0.001). Scores were determined from GUS histological staining on samples of 7–10 explants from 8 experiments and 11 levels of cysteine. The scores were based on the following ranking system: 0=no GUS$^+$ foci on explant; 2=less than ½ of explants have discrete foci on the cot-node region (<10); 4=more than ½ of the explants have <20 foci at the cot-node region; 6=more than ¾ of the explants have >20 foci at the cot-node region; 8=more than ¾ of the explants have significant staining at the hypocotyl, the entire cot-node region, and on the cotyledons; and 10=all explants have extensive staining on the hypocotyl, cot-node region, and cotyledons, including areas of complete staining. Standard errors between experiments are represented by [⊥] above each cysteine treatment (0 mg/l r=13; 400 mg/l r=12; 1000 mg/l r=4). Both treatments of 400 and 1000 mg/l cysteine significantly differ from 0 mg/l cysteine at α=0.05 (P<0.001).

The invention provides a method to enhance the transformation efficiency of plants such as legumes, e.g., soybean. In particular, the method of the invention is useful for plants that have a low efficiency of Agrobacterium-mediated transformation. A method to increase the number of transformants will also increase the overall efficiency of preparing transgenic plants. Therefore, the invention provides a method for the genetic modification of plants, both monocots and dicots, via Agrobacterium-mediated or other methods, e.g., particle gun, gene transfer. Preferred monocots include asparagus, barley, maize (*Zea mays*), oats, orchardgrass, rice, rye, sorghum (*Sorghum bicolor*), sugar cane (Saccharum spp), tall fescue (*Festuca arundinacea*), turfgrass (*Agrostis palustris*), and wheat (*Triticum aestivum*), while preferred dicots include legumes, e.g., soybean, sunflower, Brassica, safflower, cotton, sugar beet, potato, Arabidopsis, hemp and buckwheat. Legumes include, but are not limited to, large seeded legumes, pea, Arachis, e.g., peanuts, Vicia, e.g., crown vetch, hairy vetch, adzuki bean, mung bean, fava bean, and chick pea, Lupinus, e.g., lupine, trifolium, Phaseolus, e.g., common bean and lima bean, Pisum, e.g., field bean, black bean, Melilotus, e.g., clover, Medicago, e.g., alfalfa, Lotus, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

Definitions

As used herein, "genetically modified" or "transgenic" means a plant cell, plant part, plant tissue or plant which comprises a preselected DNA sequence which is introduced into the genome of a plant cell, plant part, plant tissue or plant by transformation. The term "wild type" or "native" refers to an untransformed plant cell, plant part, plant tissue or plant, i.e., one where the genome has not been altered by the presence of the preselected DNA sequence.

As used herein, "plant" refers to either a whole plant, a plant tissue, a plant part, such as pollen or an embryo, a plant cell, or a group of plant cells. The class of plants which can be used in the method of the invention is generally as broad as the class of plants amenable to transformation techniques, including both monocotyledonous and dicotyledonous plants.

The terms "heterologous," "introduced," "foreign" or "transgenic" DNA or gene refer to a recombinant DNA sequence or a gene that does not occur naturally in the genome of the plant that is the recipient of the recombinant DNA sequence or gene, or that occurs in the recipient plant at a different location or association in the genome than in the untransformed plant.

As used herein, the term "recipient cells" refers to cells that are receptive to transformation and subsequent regeneration into stably transformed, preferably fertile, plants and subsequent generation of stably transformed, fertile progeny plants. The plants are fertile in the sense that they can transmit the foreign DNA or transgenes through a complete sexual cycle to subsequent generations of progeny.

Recipient cell targets include, but are not limited to, meristem cells, Type I, Type II, and Type III callus, immature embryos and gametic cells such as microspores, pollen, sperm, ovules, megaspore, and egg cells, and preferably cotyledonary explants. Type I, Type II, and Type III callus may be initiated from tissue sources including, but not limited to, immature embryos, seedling apical meristems, axillary meristems, microspores and the such. Those cells which are capable of proliferating as callus are also recipient cells for genetic transformation. Any cell from which a fertile transgenic plant may be derived may be used as a recipient cell. Recipient cells may be somatic cells. Somatic cells are those cells of the plant which, during the normal course of development of the plant, do not contribute to the reproductive processes of the plant. Embryogenic cells are one example of somatic cells which may be induced in vivo to regenerate a plant through embryo formation.

Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, nodes, cot-nodes, axillary meristem, stem apices, lateral buds, and the like) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Suitable recipient cultures can be initiated from a number of whole plant tissue explants. For example, for maize, the tissue explants include, but not limited to, immature embryos, leaf bases, immature tassels, anthers, microspores, and other tissues containing cells capable of in vitro proliferation and regeneration of fertile plants. Other sources include nodes, cot-nodes, axillary meristems, seedling apical meristem, meristem cultures, organogenic cultures, floral meristems, and developing flowers.

For Medicago species, seed may be employed, and for Arabidopsis, non-tissue culture sources include ovules, eggs and floral meristem.

As used herein, "plant medium" refers to any medium used in the art for supporting viability and growth of a plant cell or tissue, or for growth of whole plant specimens. Such media commonly include defined components including, but not limited to: macronutrient compounds providing nutritional sources of nitrogen, phosphorus, potassium, sulfur, calcium, magnesium, and iron; micronutrients, such as boron, molybdenum, manganese, cobalt, zinc, copper, chlorine, and iodine; carbohydrates (preferably maltose for barley, although sucrose may be better for some species); vitamins; phytohormones; selection agents (for transformed cells or tissues, e.g., antibiotics or herbicides); and gelling agents (e.g., agar, Bactoagar, agarose, Phytagel, Gelrite, etc.); and may include undefined components, including, but not limited to: coconut milk, casein hydrolysate, yeast extract, and activated charcoal. The medium may be either solid (e.g., agar based or a powder) or liquid. Any conventional plant culture medium can be supplemented with an agent of the invention including basal plant culture media available from Sigma (St. Louis, Mo.) and other vendors in a dry (powdered) form for reconstitution with water. For example, media to which the agents of the invention, in aqueous or powder form, may be added include, but are not limited to, Anderson's basal salt mixture, Cape Sunder/Venus fly trap multiplication medium, Carrot callus initiation medium, Carrot shoot development medium, Chu's N6 vitamin solution, Chu's N6 basal salt mixture, Chu's N6 basal salt medium with vitamins, DCR basal salt mixture, DKW basal salt mixture with sucrose, DKW basal salt mixture (with or without sucrose), Ericksson's vitamin solution, ferrous sulfate/chelate stock solution, Gamborg's vitamin mixture, Gamborg's B5 basal salt medium, Gamborg's basal salt mixture, Guesshoff and Dox basal salt mixture, Faagland's modified basal salt mixture, Heller's basal salt mixture, Hosta initiation/multiplication medium, Hosta multiplication medium, Hosta rooting medium, Knudson orchid medium, Lindeman's modified orchid basal medium, Linsmaier and Skoog basal medium, Lloyd and McCain's woody plant basal mixture, Lloyd and McCain's WPM micronutrient mixture, Malmgren's modified terrestrial orchid mixture, Murashige and Skoog basal medium with Gamborg's vitamins, Murashige and Skoog basal salt mixture, Murashige and Skoog basal medium, Murashige and Skoog micronutrient stock, Murashige and Skoog micronutrient stock, Murashige and Skoog modified basal medium, Murashige and Skoog modified basal salt mixture, Murashige and Skoog modified basal medium with benzylaminopurine, Murashige and Skoog vitamin mixture, Murashige and Skoog modified vitamin mixture, Murashige and Skoog modified vitamin solution, Murashige and Skoog modified basal medium 2iP, Murashige and Skoog modified basal medium with kinetin, Murashige African violet/gloxinia multiplication medium, Murashige BC potato medium, Murashige begonia multiplication medium, Murashige caltaleya orchid multiplication medium, Murashige fern multiplication medium, Murashige gerbera multiplication medium, Murashige kalanchoe multiplication medium, Murashige lily multiplication medium, NB basal medium, Nitsch and Nitsch basal salt mixture, Nitsch and Nitsch vitamin mixture, Orchid multiplication medium with agar Mother, Flask IV, Orchid maintenance/replate medium without charcoal, Orchid maintenance medium, Orchid seed sowing medium with agar, Mother Flasking Medium II, Orchid maintenance/replate medium with banana replate medium, Phytotech™ orchid replate medium, Replate medium II, Orchid multiplication medium, Quorin and Lepoivre basal salt mixture, Rose initiation (stage 1) medium, Rose multiplication (stage II) medium, Schenk & Heldebrandt basal salt mixture, Terrestrial orchid medium, Vacin and Went modified basal salt mixture, Vacin and Went modified basal salt medium, Vacin and Went modified basal salt Mother Flasking Medium 1, and White's basal salt mixture.

I. DNA Constructs for Use in the Methods of the Invention

The introduced DNA includes, but is not limited to, DNA from plant genes, and non-plant genes such as those from bacteria, yeasts, animals or viruses. The introduced DNA can include modified genes, portions of genes, or chimeric genes, including genes from the same or different plant genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of an untransformed plant.

An isolated and purified DNA segment, molecule or sequence can be identified and isolated by standard methods, as described by Sambrook et al. (1989). The isolated and purified DNA segment can be identified by methods known to those of skill in the art.

Generally, the DNA is in the form of chimeric DNA, such as plasmid DNA, that can also contain coding regions flanked by regulatory sequences which promote the expression of the recombinant DNA present in the resultant plant (an "expression cassette"). For example, the DNA may itself comprise or consist of a promoter that is active in the plant but which is derived from a source that is different than the specific plant, or may utilize a promoter already present in the plant genotype.

Ultimately, the most desirable DNA segments for introduction into a plant genome may be homologous genes or gene families which encode a desired trait (e.g., increased yield per acre) and which are introduced under the control of novel promoters or enhancers, etc., or perhaps even homologous or tissue-specific (e.g., root-, collar/sheath-, whorl-, stalk-, earshank-, kernel- or leaf-specific) promoters or control elements.

1. Promoters and Other Transcription Initiation Regulatory Sequences

Preferably, the expression cassette of the invention is operably linked to a promoter, which provides for expression of a linked DNA sequence. The DNA sequence is operably linked to the promoter when it is located downstream from the promoter, to form an expression cassette. An isolated promoter sequence that is a strong promoter for heterologous DNAs is advantageous because it provides for a sufficient level of gene expression to allow for easy detection and selection of transformed cells and provides for a high level of gene expression when desired. Plant promoter sequences can be constitutive or inducible, environmentally- or developmentally-regulated, or cell- or tissue-specific.

Preferred expression cassettes will generally include, but are not limited to, a plant promoter such as the CaMV 35S promoter (Odell et al., 1985), the enhanced CaMV 35S promoter, the Figwort Mosaic Virus (FMV) promoter (Richins et al., 1987), the mannopine synthase (mas) promoter, the octopine synthase (ocs) promoter, or others such as the promoters from CaMV 19S (Lawton et al., 1987), nos (Ebert et al., 1987), Adh (Walker et al., 1987), sucrose synthase (Yang et al., 1990), α-tubulin, ubiquitin, actin (Wang et al., 1992), cab (Sullivan et al., 1989), PEPCase (Hudspeth et al., 1989) or those associated with the R gene complex (Chandler et al., 1989).

Other useful inducible promoters include heat-shock promoters (Ou-Lee et al., 1986; Ainley et al., 1990), a nitrate-inducible promoter derived from the spinach nitrite reductase gene (Back et al., 1991), hormone-inducible promoters (Yamaguchi-Shinozaki et al., 1990; Kares et al., 1990), and light-inducible promoters associated with the small subunit of RuBP carboxylase and LHCP gene families (Kuhlemeier et al., 1989; Feinbaum et al., 1991; Weisshaar et al., 1991; Lam and Chua, 1990; Castresana et al., 1988; Schultze-Lefert et al., 1989). Examples of useful tissue-specific, developmentally-regulated promoters include the β-conglycinin 7S promoter (Doyle et al., 1986; Slighton and Beachy, 1987), and seed-specific promoters (Knutzon et al., 1992; Bustos et al., 1991; Lam and Chua, 1991; Stayton et al., 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., 1991), phaseolin, zein, soybean trypsin inhibitor, ACP, stearoyl-ACP desaturase, and oleosin. Seed-specific gene regulation is discussed in EPA 255 378. Promoter hybrids can also be constructed to enhance transcriptional activity (Hoffman, U.S. Pat. No. 5,106,739), or to combine desired transcriptional activity and tissue specificity.

Further suitable promoters include inducible promoters, such as the light inducible promoter derived from the pea rbcS gene (Coruzzi et al., 1971), the actin promoter from rice (McElroy et al., 1990), and water-stress-, ABA-and turgor-inducible promoters (Skriver et al., 1990); Guerrero et al., 1990), tissue-specific promoters, such as root-cell promoters (Conkling et al., 1990), and developmentally-specific promoters such as seed specific promoters, e.g., the phaseolin promoter from beans (Sengupta-Gopalan, 1985), and the Z10 and Z27 promoters from maize. Tissue specific expression may also be functionally accomplished by introducing a constitutively expressed gene (all tissues) in combination with an antisense gene that is expressed only in those tissues where the gene product is not desired.

Promoters which direct specific or enhanced expression in certain plant tissues are known to those of skill in the art. These include, for example, the rbcS promoter, specific for green tissue; the ocs, nos and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm. Transcription enhancers or duplications of enhancers can be used to increase expression from a particular promoter (see, for example, Fromm et al., 1989). Examples of such enhancers include, but are not limited to, elements from the CaMV 35S promoter and octopine synthase genes (Last et al., U.S. Pat. No. 5,290,924). The 16 bp ocs enhancer element from the octopine synthase (ocs) gene (Ellis et al., supra (1987); Bouchez et al., 1989), especially when present in multiple copies, can be used to achieve enhanced expression in roots.

Other promoters useful in the practice of the invention are known to those of skill in the art. For example, see Van Ooijen et al. (U.S. Pat. No. 5,593,963) and Walsh et al. (U.S. Pat. No. 5,743,477).

A leader sequence can also be incorporated into the gene transfer construct of the present invention. Preferred leader sequences include those which comprise sequences selected to direct optimum expression of the attached gene, i.e., to include a preferred consensus leader sequence which can increase or maintain mRNA stability and prevent inappropriate initiation of translation (Joshi, 1987). Such sequences are known to those of skill in the art. Sequences that are derived from genes that are highly expressed in plants are most preferred.

Regulatory elements such as Adh intron 1 (Callis et al., 1987), sucrose synthase intron (Vasil et al., 1989), rice actin 1 intron 1 (McElroy et al., 1991) or TMV omega element (Gallie et al., 1989) can also be included where desired. Other such regulatory elements useful in the practice of the invention are known to those of skill in the art.

An isolated and purified DNA segment can be combined with the transcription regulatory sequences by standard methods as described in Sambrook et al., cited supra, to yield an expression cassette. Briefly, a plasmid containing a promoter such as the 35S CaMV promoter can be constructed as described in Jefferson, 1987) or obtained from Clontech Lab in Palo Alto, Calif. (e.g., pBI121 or pBI221). Typically, these plasmids are constructed to provide for multiple cloning sites having specificity for different restriction enzymes downstream from the promoter. The isolated and purified DNA segment can be subcloned downstream from the promoter using restriction enzymes to ensure that the DNA is inserted in proper orientation with respect to the promoter so that the DNA can be expressed. Once the isolated and purified DNA segment is operably linked to a promoter, the expression cassette so formed can be subcloned into a plasmid or other vectors.

2. Targeting Sequences

Additionally, expression cassettes can be constructed and employed to target the product of the isolated and purified DNA sequence or segment to an intracellular compartment within plant cells or to direct a protein to the extracellular environment. This can generally be achieved by joining a DNA sequence encoding a transit or signal peptide sequence to the coding sequence of the isolated and purified DNA sequence. The resultant transit, or signal, peptide will transport the protein to a particular intracellular, or extracellular destination, respectively, and can then be post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. Nos. 5,258,300 and 5,593,963.

The isolated and purified DNA segment can be directed to a particular organelle, such as the chloroplast rather than to the cytoplasm. Thus, the expression cassette can further be comprised of a chloroplast transit peptide encoding DNA sequence operably linked between a promoter and the isolated and purified DNA segment (for a review of plastid targeting peptides, see Heijne et al., 1989; Keegstra et al., 1989). This is exemplified by the use of the rbcS (RuBISCO) transit peptide which targets proteins specifically to plastids.

An exogenous chloroplast transit peptide can be used. A chloroplast transit peptide is typically 40 to 70 amino acids in length and functions post-translationally to direct a protein to the chloroplast. The transit peptide is cleaved either during or just after import into the chloroplast to yield the mature protein. The complete copy of the isolated and purified DNA segment may contain a chloroplast transit peptide sequence. In that case, it may not be necessary to combine an exogenously obtained chloroplast transit peptide sequence into the expression cassette.

Exogenous chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences include, but are not limited to, the small subunit of ribulose biphosphate carboxylase, ferredoxin, chlorophyll a/b binding protein, chloroplast ribosomal proteins encoded by nuclear genes, certain heat shock proteins, amino acid biosynthetic enzymes such as acetolactate acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above. Furthermore, the transit peptide may compromise sequences derived from transit peptides from more than one source and may include a peptide sequence derived from the amino-terminal region of the mature protein which in its native state is linked to a transit peptide.

Regardless of the source of the DNA fragment coding for the transit peptide, it should include a translation initiation codon and an amino acid sequence that is recognized by and will function properly in chloroplasts of the host plant. Attention should also be given to the amino acid sequence at the junction between the transit peptide and the protein encoded by the isolated and purified DNA segment where it is cleaved to yield the mature enzyme. Certain conserved amino acid sequences have been identified and may serve as a guideline. Precise fusion of the transit peptide coding sequence with the isolated and purified DNA segment coding sequence may require manipulation of one or both DNA sequences to introduce, for example, a convenient restriction site. This may be accomplished by methods including site-directed mutagenesis, insertion of chemically synthesized oligonucleotide linkers, and the like.

Once obtained, the chloroplast transit peptide sequence can be appropriately linked to the promoter and the isolated and purified DNA segment in an expression cassette using standard methods. Briefly, a plasmid containing a promoter functional in plant cells and having multiple cloning sites downstream can be constructed as described in Jefferson, cited supra. The chloroplast transit peptide sequence can be inserted downstream from the promoter using restriction enzymes. The isolated and purified DNA segment can then be inserted immediately downstream from and in frame with the 3' terminus of the chloroplast transit peptide sequence so that the chloroplast transit peptide is linked to the amino terminus of the protein encoded by the isolated and purified DNA segment. Once formed, the expression cassette can be subcloned into other plasmids or vectors.

Targeting of the gene product to an intracellular compartment within plant cells may also be achieved by direct delivery of an isolated and purified DNA segment to the intracellular compartment. For example, an expression cassette encoding a protein, the presence of which is desired in the chloroplast, may be directly introduced into the chloroplast genome using the method described in Maliga et al., U.S. Pat. No. 5,451,513.

It may be useful to target DNA itself within a cell. For example, it may be useful to target an introduced isolated and purified DNA to the nucleus as this may increase the frequency of transformation. Nuclear targeting sequences that function in plants are known, e.g., the Agrobacterium virD protein is known to target DNA sequences to the nucleus of a plant cell. Within the nucleus itself, it would be useful to target a gene in order to achieve site-specific integration. For example, it would be useful to have a gene introduced through transformation replace an existing gene in the cell.

3. 3' Sequences

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens* (Bevan et al., 1983), the terminator for the T7 transcript from the Agrobacterium tumefaciens, T-DNA and the 3' end of the protease inhibitor I or II genes from potato or tomato, although other 3' elements known to those of skill in the art can also be employed. These 3' nontranslated regulatory sequences can be obtained as described in *Methods in Enzymology* (1987) or are already present in plasmids available from commercial sources such as Clontech (Palo Alto, Calif.). The 3' nontranslated regulatory sequences can be operably linked to the 3' terminus of the isolated and purified DNA segment by standard methods.

4. Marker Genes

In order to improve the ability to identify transformants, one may desire to employ one or more selectable marker genes or reporter genes as, or in addition to, the expressible isolated and purified DNA segment(s). "Marker genes" or "reporter genes" are genes that impart a distinct phenotype to cells expressing the marker gene and thus allow such transformed cells to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Of course, many examples of suitable marker genes or reporter genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements. See, for example, Steifel et al. (1990) and Keller et al. (1989).

Elements of the present disclosure are exemplified in detail through the use of particular marker genes. However in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed monocot.

a. Selectable Markers

Possible selectable markers for use in connection with the present invention include, but are not limited to, a neo gene (Potrykus et al., 1985) which codes for kanamycin resistance and can be selected for using kanamycin, G418, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) or acetoacid synthase gene (AAS) which confers resistance to imidazolinone, sulfonylurea or other ALS-inhibiting chemicals (European Patent Application 154,204, 1985); a methotrexate-resistant DHFR gene (Thillet et al.,1988); a dalapon dehalogenase gene that confers resistance to the herbicide dalapon (U.S. Pat. No. 5,780,708); or a mutated anthranilate synthase gene that confers resistance to 5-methyl tryptophan (WO 97/26366). Where a mutant EPSP synthase gene is employed, additional benefit may be realized through the incorporation of a suitable chloroplast transit peptide, CTP (U.S. Pat. No. 4,940,835). See also, Lundquist et al., U.S. Pat. No. 5,508, 468.

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals (Potrykus, 1989).

b. Screenable Markers or Reporter Genes

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a βlactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an αamylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

5. Transgenes for Plant Modification

The present invention provides methods and compositions for the transformation of plant cells with genes in addition to, or other than, marker genes. Such transgenes will often be genes that direct the expression of a particular protein or polypeptide product, but they may also be non expressible DNA segments, e.g., transposons such as Ds that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; mycotoxin reduction or elimination; increased yields; food or feed content and makeup; grain composition or quality; physical appearance; male sterility; drydown; standability; prolificacy; starch properties; oil quantity and quality; and the like. One may desire to incorporate one or more genes conferring any such desirable trait or traits, such as, for example, a gene or genes encoding herbicide resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. Thus, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired. to proteins.

6. Other sequences

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

One vector that is useful for expression in both plant and prokaryotic cells is the binary Ti plasmid (as disclosed in Schilperoort et al., U.S. Pat. No. 4,940,838) as exemplified by vector pGA582. This binary Ti vector can be replicated in prokaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells. Construction of Agrobacterium transformation vectors is well known to the art. See, for example, Rogers et al., 1986; Rogers et al., 1987a; Rogers et al., 1987b; and Deblaere et al., 1987). These vectors can be employed to inset a selected chimeric plant gene to an explant susceptible to infection by Agrobacterium. Vectors are introduced into Agrobacterium by triparental mating (Ditta et al., 1980), which is then used for the transformation of plants, e.g., canola (Fry et al., 1987; Radke et al., 1988) or soybean (Hinchee et al., 1988). Preferred vectors include a marker gene and a selectable marker gene, each operably linked to transcription regulatory elements, e.g., promoters and transcription termination signals.

Vectors, plasmids, cosmids, YACs (yeast artificial chromosomes) and DNA segments for use in transforming such cells will, of course, generally comprise the isolated and purified cDNA(s), isolated and purified DNA(s) or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

II. DNA Delivery of DNA Molecules to Host Cells

The present invention generally includes steps directed to introducing an isolated and purified DNA sequence, such as an isolated and purified cDNA, into a recipient cell to create a transformed cell. It is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Cells of the plant tissue source are preferably embryogenic cells or cell-lines that can regenerate fertile transgenic plants and/or seeds. The cells can be derived from either monocotyledons or dicotyledons. Suitable examples of plant species include wheat, rice, Arabidopsis, tobacco, maize, soybean, oat, and the like.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells.

The transformation is carried out under conditions directed to the plant tissue of choice. The plant cells or tissue are exposed to the DNA carrying the isolated and purified DNA sequences for an effective period of time. This may range from a few minutes to a 2–3 day co-cultivation in the presence of plasmid-bearing Agrobacterium cells. Buffers and media used will also vary with the plant tissue source and transformation protocol. Many transformation protocols employ a feeder layer of suspension culture cells (tobacco or Black Mexican Sweet corn, for example) on the surface of solid media plates, separated by a sterile filter disk from the plant cells or tissues being transformed.

The following provide exemplary methods to transform canola and soybean. However, the methods of the invention are not limited to canola and soybean, but may be employed with any plant cell, part or tissue that is susceptible to Agrobacterium-mediated infection.

1. Canola Transformation

Plant Material

Stock plants are produced from seeds of the Westar variety planted in Metro Mix 350 and germinated in a growth chamber under a day temperature of 15° C., a night temperature of 10° C., a 16 hour day/8 hour night illumination period, a light intensity of 600 $\mu$En m$^{-2}$s$^{-1}$, and 50% relative humidity. Seedlings are subirrigated with water daily, and soaked with a 15-30-15 nutrient solution every other day for one hour. At three weeks, seedlings are transferred into 6" pots. Five week old plants are harvested once the plants bolted, but prior to flowering (plants with up to three flowers can be employed, however). The leaves and buds are removed from the stem, and the 4–5 inches of stem just below the flower buds are used as the explant tissue source. Just prior to inoculation, the stems were sterilized by soaking in 70% ethanol for 1 minute, 38% Chlorox (4% sodium hypochlorite) for 20 minutes, rinsing two times in sterile deionized water, and soaking in two tablespoons of Captan (Captan 50-WP, ICI Ag Products) plus 500 mls sterile water for 15 minutes.

Preparation of Agrobacterium

Five to 7 days prior to inoculation, Agrobacterium is streaked from a frozen glycerol stock onto an LB plate (1.5% agar) containing 100 mg/l spectinomycin, 100 mg/l streptomycin, 25 mg/l chloramphenicol, and 50 mg/l kanamycin (denoted LBSSCK). Two days before inoculation day, a 10 $\mu$l loop of Agrobacterium is placed into a tube containing 2 mls of LBSSCK and placed on a rotator overnight at 22–28° C. The day before inoculation, the Agrobacterium is subcultured by placing 200 $\mu$l in a tube containing 2 ml of fresh LBSSCK, which is placed on a rotator overnight. On the day of inoculation, the Agrobacterium was diluted 1:10 with MS liquid medium (Murashige and Skoog, 1962) to an OD$_{660}$ of 0.2–0.4.

Explant Inoculation

Sterilized stems are cut into 0.6 cm segments (0.3–1.5 cm segments can be used), noting their basal orientation. Explants are inoculated for five minutes in a square Petri plate (100×15 mm) with the 1:10 dilution of Agrobacterium. Five mls of Agrobacterium solution are added to five stems by pipetting the Agrobacterium directly on top of the explants. After five minutes, the Agrobacterium solution is aspirated off the explants. The stem explants are then cultured in the basal-side down orientation for an optimal shoot regeneration response on the co-culture plates. Co-culture plates (100×15 mm) containing 1/10 MS salts (this can range from about 1/10 to full strength; Gibco, 500-1117EH), 1×B5 vitamins (Sigma, G-2519), 0.5 mg/l 6-benzylaminopurine (this can range from about 0.1–2 mg/l), 3% sucrose (this can range from about 1–6%), pH 5.7, solidified with 0.9% agar, covered with 2 ml TXD liquid medium (Horsch et al., 1985) onto which an 8.5 cm piece of sterile Whatman qualitative grade filter paper is placed. Excess Agrobacterium present on the stem explants placed on the filter paper is blotted off using another piece of sterile 8.5 cm filter paper. The co-culture plates are placed in clear plastic bags which are slit on the sides to permit air exchange, and which are incubated in a warm room at 25° C. under 24 hours continuous cool white light (40 $\mu$En m$^{-2}$s$^{-1}$).

Tissue Selection and Regeneration

After two days, the stem explants are moved onto MS medium containing 500 mg/l ticarcillin, 50 mg/l cefotaxime, and 1 mg/l 6-benzylaminopurine for a three day delay period. Plates are again placed in slit, clear plastic bags which are placed in the warm room. After a three day delay period, stem explants are moved onto glyphosate selection medium containing MS salts, B5 vitamins, 0.1 mM glyphosate (this can range from about 0.025–0.2 mM), 500 mg/l ticarcillin (this can range from about 250–750 mg/l), 50 mg/l cefotaxime (this can range from about 25–100 mg/l), and 1 mg/l 6-benzylaminopurine (this can range from about 0.1–4 mg/l) for three weeks. After three weeks, the stem explants are moved onto glyphosate selection medium containing MS salts, B5 vitamins, 0.1 mM glyphosate (this can range from about 0.025–0.2 mM), 500 mg/l ticarcillin (this can range from about 250–750 mg/l), 50 mg/l cefotaxime (this can range from about 25–100 mg/l), and 1 mg/l 6-benzylaminopurine (this can range from about 0.1–4 mg/l), plus 0.5 mg/l gibberellic acid A3 (this can range from about 0.1–2 mg/i), which enhances shoot elongation, for another three week period. After these six weeks on glyphosate selection medium, normally developing green shoots are excised from the stem explants. Shoots (4–5 per plate) are placed in rooting medium (1/10-full strength MS salts, Staba vitamins (Staba, 1969), 3% sucrose (this can range from about 1–6%), 500 mg/l ticarcillin (this can range from about 250–750 mg/l), 50 mg/l cefotaxime (this can range from about 25–100 mg/l), and 2 mg/l indolebutyric acid (this can range from about 0.5–3 mg/l), pH 5.7, solidified with 0.9% agar. Root development begins to occur as early as one week after shoots are placed on rooting medium. At the two week timepoint, shoots having a large root base are moved into 2½" pots containing Metro Mix 350 (Hummert Co., St. Louis, Mo.). Flats are covered with clear plastic domes (Hummert Co., St. Louis) so the shoots elongate. Flats containing RO plants are placed in a growth chamber under the same conditions as described above for stock plant growth. After 3–4 days, the domes are cracked in order to harden off the plants under the following conditions: Temperature: 20° C. day/15° C. night; Photoperiod: 16 hour light/8 hour dark; Light intensity: 450 $\mu$En m$^{-2}$s$^{-1}$; Relative humidity: 70%; Fertilizer: 15-16-17 Peter's Solution (200 ppm nitrogen). Hardened plants are grown for approximately 14 weeks under the same conditions, at which time seeds are collected. Cross-pollination is prevented by bagging the plants at bolting time.

This protocol results in transformation efficiencies (defined as the number of confirmed transgenics/the number of explants inoculated, expressed as a percentage) as high as 35–40%. This is a significant improvement over the protocol using kanamycin selection (Fry et al., 1987).

2. Soybean Transformation

Plant Material

Seeds of soybean are surface sterilized by rinsing them in dilute Tween 20 (polyoxyethylenesorbitan monolaurate) for 30 seconds, followed by rinsing under running tap water for approximately two minutes. The seeds are then rinsed in 80% ethanol, and then agitated in freshly made 50% Chlorox (5.25% sodium hypochlorite) containing Tween 20 for 15 minutes. The seeds are then completely rinsed with five rinses of sterile distilled water. They are then placed in a saturated Captan and/or Benylate slurry for 2–30 minutes to control fungus infestation.

Sterilized seeds are then placed on 0.7% purified agar-solidified B5 basal medium (Gamborg et al., 1968) for germination (approximately 15 seeds per plate). The petri dishes are placed in a plastic bag slit on the sides to permit air exchange, and incubated in a culture room under 18–20 hours light (60 $\mu$En m$^{-2}$s$^{-1}$), 4–6 hrs dark, at 25° C., for 5–6 days. After this incubation, the germinated seeds are placed in a cold room or refrigerator (0–10° C.; average temperature of 4° C.) for at least 24 hours prior to explanting.

Preparation of Agrobacterium

Agrobacterium strains to be used for transformation are prepared as follows. Bacteria are streaked from frozen glycerol stocks onto LBSCK plates containing 1.5% agar-solidified LB medium plus 100 mg/l of spectinomycin, 25 mg/l of chloramphenicol, and 50 mg/l of kanamycin. The bacteria can be incubated at room temperature or in an incubator at 27° C. for 2–4 days. Prior to preparing the Agrobacterium inoculum, a fresh plate of Agrobacterium is streaked from the first plate 2–3 days prior to growth on liquid medium. One to two days prior to the inoculation of soybean explants, one loop of bacteria is transferred from a freshly streaked plate into a culture tube containing 2 ml of YEP medium containing 10 g/l peptone, 10 g/l yeast extract, 5 g/l NaCl, 100 mg/l spectinomycin, 25 mg/l chloramphenicol, and 50 mg/l kanamycin. Larger volumes of bacteria can be grown using the same basic formula of one loop of bacteria per 2 ml of YEP. The tube containing the bacteria in YEP is vortexed to disperse the clump of bacteria, and placed on a rotator. For a one day culture, the bacteria can be started at about 7:00 a.m.; for a two day culture, the bacteria can be started later in the day and allowed to grow overnight. The afternoon prior to inoculating the explants, 4–6 mls (2–3 tubes) of the bacterial culture are added to 50 mls of AB minimal salts medium (Chilton et al., 1974) containing the same concentrations of spectinomycin, chloramphenicol, and kanamycin as in the LBSCK medium, in sterile 250 ml flasks. This culture is grown on a shaker overnight at 28° C. The bacteria are pelleted by centrifugation and the pellet is resuspended to an $OD_{660}$ of 0.25–1.0 with the following medium: 1/10 B5 salts (this can range from about 1/10 to full strength), 1/10 B5 vitamins (this can range from about 1/10 to full strength), 3% sucrose or glucose (this can range from about 0.5–6% sucrose or glucose), 7.5 $\mu$M 6-benzyl-aminopurine (this can range from about 2.5–20 $\mu$M), 200 $\mu$M acetosyringone (this can range from about 50–300 $\mu$M), 1 mM galacturonic acid (this can range from about 0.1–2 mM), 0.25 mg/l gibberellic acid (GA3) (this can range from 0–0.5 mg/l), and 20 mM MES, pH 5.4 (the pH can range from about 5.2–6.0).

Explant Inoculation

Explants are prepared by removing the seed coat from the germinated seedlings and cutting the hypocotyl at approximately 0.5 cm or more from the cotyledons (one cm is preferred). The lower portion of the hypocotyl and root axis is discarded. The cotyledons and remaining hypocotyl are completely split by making an incision down the middle of the hypocotyl and then bending the halves apart so that they separated from one another. The primary leaves and primary shoot meristem are removed. The region of the cotyledon near the axillary bud is wounded multiple times (anywhere from 3–15 times) using a scalpel blade, the score marks being placed longitudinally with respect to the embryo axis. The axillary bud can be damaged in the process, but this is not required. Approximately 40–80 explants are prepared and added to a single, dry petri dish. Approximately 10 mls of the bacterial inoculum are added to just cover the explants. The explants remain in contact with the Agrobacterium solution for about 30 minutes. The Agrobacterium solution is then removed from the explants which are briefly blotted on sterile Whatman filter paper prior to being placed flat (adaxial) side down onto co-culture plates. Co-culture plates are prepared by adding 4–5 mls of the bacterial dilution medium additionally containing 3% sucrose, 1 mM galacturonic acid, and 200 $\mu$M acetosyringone to 1–2 layers of sterile Whatman filter paper in a 100×15 mm petri dish. The co-culture medium can contain a mixture of 0.5–6% glucose or 0.5–6% sucrose (1–3% of either being preferred), with or without 0.1–10 mM galacturonic acid (1 mM being preferred), with or without 50–300 $\mu$M acetosyringone (100–200 $\mu$M being preferred). The co-culture medium is solidified with 0.8% washed agar (Sigma, A 8678).

Tissue Selection and Regeneration

The explants are co-cultured with the Agrobacterium in a culture room at 20–23° C. under an 18–20 hour light/4–6 hour dark photoperiod (co-culturing can be carried out from about 18–26° C.). Co-culture lasts for 2–4 days. After co-culture, the explants are washed in wash medium containing 1/10 B5 salts (this can range from about 1/10 to full strength), 1/10 B5 vitamins (this can range from about 1/10 to full strength), 7.5 $\mu$M 6-benzylaminopurine (this can range from about 2.5–20 EM), pH 5.6 (the pH can range from about 5.2–6.0), 500 mg/l ticarcillin (this can range from about 250–750 mg/l), and 100 mg/l cefotaxime (this can range from about 25–200 mg/l).

The washed explants are cultured on a culture medium containing B5-basal salts and vitamins, 7.5 $\mu$M 6-benzylaminopurine (this can range from about 2.5 $\mu$M-20 $\mu$M), 500 mg/l ticarcillin (this can range from about 250–750 mg/l), 100 mg/l cefotaxime (this can range from about 25–200 mg/l), and 0.075–0.1 mM glyphosate (this can range from about 0.025–0.4 mM). The plates are sealed with white 3M porous tape and placed in a culture room or incubator at 24–26° C. under an 18–20 hour light/4–6 hour dark cycle at 20–80 μEn m$^{-2}$s$^{-1}$. Subsequent subcultures are made every 2–3 weeks.

At two to four weeks, the cultures are transferred to MSB5 medium (Sigma, M 0404 or Gibco, 500-117EH plus Sigma, G2519) or B5 basal medium plus 1 mg/l zeatin riboside (this can range from about 0–5 mg/l), 0.5 mg/l gibberillic acid (GA3) (this can range from about 0–2 mg/l), 0.1 mg/l indoleacetic acid (this can range from about 0–1 mg/l), 2.5 μM 6-benzylaminopurine (this can range from about 0–5 μM), 500 mg/l ticarcillin (this can range from about 250–750 mg/l), 100 mg/l cefotaxime (this can range from about 25–200 mg/l), and 0.075 mM glyphosate (this can range from about 0.025–0.2 mM). Additional B5 micronutrients (up to four times the standard concentration of each micronutrient alone or in various combinations with the others) and 2 gm/l proline (this can range from about 0–2 gm/l) can be added to this medium.

At the four to six week time point, the petiole/hypocotyl tissue and cotyledons, as well as any dead or dying material, i.e., any non-regenerating tissues, are removed (such material can generally be removed between 4–9 weeks). The regenerating cultures are transferred to 0.8% washed agar-solidified elongation medium comprising MSB5 medium or B5 basal medium plus 1 mg/l zeatin riboside (this can range from about 0–5 mg/l), 0.5 mg/l gibberillic acid (this can range from about 0–2 mg/l), 0.1 mg/l indoleacetic acid (this can range from about 0–1 mg/l), 500 mg/l ticarcillin (this can range from about 250–750 mg/l), 100 mg/l cefotaxime (this can range from about 25–200 mg/l), and 0.05 mM glyphosate (this can range from about 0.025–0.2 mM), and again placed in a culture room or incubator at 24–26° C. under an 18–20 hour light/4–6 hour dark cycle at 20–80 μEn m$^{-2}$s$^{-1}$. Elongation medium can contain about 0.25–2 mg/l zeatin riboside, 0.01–1 mg/l indoleacetic acid, and 0.1–5 mg/l gibberellic acid (GA3). Cultures are transferred every three weeks to the same medium. Identification of putative transgenics (elongating, normal appearing shoots) requires approximately 8–20 weeks.

Shoots are rooted on 0.7% purified agar-solidified one-half or full strength MSB5 medium or one-half or full strength B5 basal medium containing 500 mg/l ticarcillin (this can range from about 0–500 mg/l), 100 mg/l cefotaxime (this can range from about 0–100 mg/l), and 1 mg/l indolebutyric acid (this can range from about 0.1–2 mg/l) or naphthaleneacetic acid (this can range from about 0.05–2 mg/l), with 0–50 mg/l glutamine and 0–50 mg/l asparagine at 24–26° C. under an 18–20 hour light/4–6 hour dark cycle for 2–6 weeks. Rooted shoots are placed in 2″ pots containing moistened MetroMix 350, and kept enclosed in magenta boxes until acclimatized at 24–26° C. under an 18–20 hour light/4–6 hour dark cycle (20–80 μEn m$^{-2}$s$^{-1}$). Shoots were hardened off for 3–4 days after cracking the lids under the following conditions: Photoperiod: 18–20 hours light/4–6 hours dark; Light intensity: 20–80 μEn m$^{-2}$s$^{-1}$; Temperature: 24–26° C. Hardened plants are grown for approximately 3 weeks under the following conditions: Photoperiod: 12 hours light/12 hours dark; Light intensity: 450 μEn m$^{-2}$s$^{-1}$; Relative humidity: 70%; Temperature: 26° C. day/21° C. night. Transformation is confirmed by detection of expression of the selectable marker or non-selectable marker. Transformed plants are subsequently grown under the following conditions: Photoperiod: 12 hours light/12 hours dark; Light intensity: 450 μEn m$^{-2}$s$^{-1}$; Relative humidity: 70%; Temperature: 26° C. day/21° C. night; Fertilizer: 15-16-17 Peter's Solution (200 ppm nitrogen). Plants are grown for approximately 11 weeks, at which time seed is collected.

Glyphosate Selection

Glyphosate (0.05 mM–0.1 mM) may be employed as a selectable marker (Hinchee et al., 1994) for both canola and soybean. Leaves of glyphosate-resistant canola and soybean transformants (designated R0 generation) are screened for GUS expression. Seeds from R0 transformed plants are assayed for other non-selectable genes.

III. Production and Characterization of Stable Transgenic Plants

After effecting delivery of an isolated and purified DNA segment to recipient cells, the next steps of the invention generally concern identifying the transformed cells for further culturing and plant regeneration. As mentioned above, in order to improve the ability to identify transformants, one may desire to employ a selectable or screenable marker gene as, or in addition to, the expressible isolated and purified DNA segment. In this case, one would then generally assay the potentially transformed cell population by exposing the cells to a selective agent or agents, or one would screen the cells for the desired marker gene trait.

A. Selection

An exemplary embodiment of methods for identifying transformed cells involves exposing the cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

The enzyme luciferase is useful as a screenable marker. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening will enable one to identify transformants in a wider variety of cell and tissue types.

B. Regeneration and Seed Production

Cells that survive the exposure to the selective agent, or cells that have been scored positive in a screening assay, may be cultured in media that supports regeneration of plants. Such media are known to the art. The transformed cells, identified by selection or screening and cultured in an appropriate medium that supports regeneration, will then be allowed to mature into plants. Developing plantlets are transferred to soilless plant growth mix, and hardened.

Plants are preferably matured either in a growth chamber or greenhouse. After the regenerating plants have reached the stage of shoot and root development, they may be transferred to a greenhouse for further growth and testing.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the isolated and purified DNA segment into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced isolated and purified DNA segment, the plant is self-pollinated at least once in order to produce a homozygous backcross converted inbred containing the isolated and purified DNA segment. Progeny of these plants are true breeding.

Alternatively, seed from transformed plants regenerated from transformed tissue cultures is grown in the field and self-pollinated to generate true breeding plants. Progenies from these plants become true breeding lines which are evaluated for a desired phenotype or trait.

Upon the identification of the superior performance of transgenic plants, the parent selections are advanced and inbred lines are produced through conventional breeding techniques. Hybrid plants having one or more parents containing the isolated and purified DNA segment are tested in commercial testing and evaluation programs and performance documented.

C. Characterization

To confirm the presence of the isolated and purified DNA segment(s) or "transgene(s)" in the regenerating plants, a variety of assays may be performed. Such assays include, for example, "molecular biological" assays well known to those of skill in the art, such as Southern and Northern blotting, RT-PCR and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced isolated and purified DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the isolated and purified DNA segment in question, they do not provide information as to whether the isolated and purified DNA segment is being expressed. Expression may be evaluated by specifically identifying the protein products of the introduced isolated and purified DNA sequences or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of isolated and purified DNA segments encoding storage proteins which change amino acid composition and may be detected by amino acid analysis.

1. DNA Integration, RNA Expression and Inheritance

Genomic DNA may be isolated from cell lines or any plant parts to determine the presence of the isolated and purified DNA segment through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether an isolated and purified DNA segment is present in a stable transformant, but does not prove integration of the introduced isolated and purified DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced isolated and purified DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced isolated and purified DNA segments in high molecular weight DNA, i.e., confirm that the introduced isolated and purified DNA segment has been integrated into the host cell genome. The technique of Southern hybridization provides information that is obtained using PCR, e.g., the presence of an isolated and purified DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of an isolated and purified DNA segment. However, it is well known in the art that dot or slot blot hybridization may produce misleading results, as probe may be non-specifically bound by high molecular weight DNA.

Both PCR and Southern hybridization techniques can be used to demonstrate transmission of an isolated and purified DNA segment to progeny. In most instances the characteristic Southern hybridization pattern for a given transformant will segregate in progeny as one or more Mendelian genes indicating stable inheritance of the gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced isolated and purified DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the isolated and purified DNA segment in question, they do not provide information as to whether the isolated and purified DNA segment is being expressed. Expression may be evaluated by specifically identifying the protein products of the introduced isolated and purified DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of isolated and purified DNA segments encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

For example, selfed $R_1$ progeny from a transgenic soybean plant are analyzed for co-segregation of the non-selectable marker gene and the selectable marker gene, e.g., GUS and NPT activity. A 3:1 segregation ratio indicates the presence of a single active T-DNA locus. Southern analysis is employed to confirm that progeny plants contain the inserted DNA fragment necessary to confer these genetic traits. Southern hybridization is performed on $R_I$ progeny to assay for the presence and copy number of the T-DNA in the plants. The progeny are also analyzed for GUS and NPTII. Plants which have GUS and NPT activity show strong hybridization with GUS and NPT probes at a level consistent with one or a few copies of the T-DNA. All of the hybridizing plants show the same pattern of putative T-DNA junction fragments indicating that there are no silent copies of the T-DNA segregating independently of the active copy. The junction fragment pattern is consistent with a single site of T-DNA insertion. A positive hybridization result and the correlation between enzyme activity and T-DNA in the $R_1$ progeny are evidence that the transgenic plant was generated by the expected Agrobacterium-mediated events.

D. Establishment of the Introduced DNA in Other Plant Varieties

Fertile, transgenic plants may then be used in a conventional plant breeding program in order to incorporate the isolated and purified DNA segment into the desired lines or varieties. Among the approaches that conventional breeding programs employ is a conversion process (backcrossing). Briefly, conversion is performed by crossing the initial transgenic fertile plant to elite inbred lines (which may or may not be transgenic to yield an $F_1$ hybrid plant). The progeny from this cross will segregate such that some of the plants will carry the isolated and purified DNA segment whereas some will not. The plants that do carry the isolated and purified DNA segment are then crossed again to the elite inbred lines resulting in progeny which segregate once more. This backcrossing process is repeated until the original elite inbred has been converted to a line containing the isolated and purified DNA segment, yet possessing all important attributes originally found in the parent. A separate backcrossing program will be generally used for every elite line that is to be converted to a genetically engineered elite line.

Generally, the commercial value of the transformed plant produced herein will be greatest if the isolated and purified DNA segment can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, drought and insect resistance. As such, it is necessary to incorporate the gene into a large number of parental lines so that many hybrid combinations can be produced containing the isolated and purified DNA segment.

Plant breeding and the techniques and skills required to transfer genes from one line or variety to another are well known to those skilled in the art. Thus, introducing an isolated and purified DNA segment, preferably in the form of recombinant DNA, into any other line or variety can be accomplished by these breeding procedures.

E. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents (e.g., oils or starches) of crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The invention will be further described by the following non-limiting example.

EXAMPLE I

Agrobacterium strains

One of two different Agrobacterium strains containing different binary plasmids were used to transform soybean explants using the cotyledonary-node (cot-node) method (see U.S. Pat. Nos. 5,942,660 and 5,959,179). A number of the experiments use Agrobacterium strain AGL1 and a binary plasmid BSF16 that contains the bar gene for selection using the herbicide Liberty® (AgroEvo™; bar encodes for phosphinothricin acetyltransferase that detoxifies phosphinothricin, "PPT", or glufosinate), the phenotypic marker uidA (gusA) gene which encodes for β-glucuronidase (GUS), and a sulfur-rich gene albumin from sunflower (Molvig et al., 1997) driven by the seed-specific promoter from the pea vicilin. The constitutive promoter, CaMV 35S, drives both the gusA and the bar gene in pBSF16. The second Agrobacterium strain, LBA4404, contains the binary plasmid pTOK233. pTOK233 contains the gusA gene under the control of the CaMV 35S promoter and the hpt gene under the control of the CaMV 35S promoter (Hiei et al., 1994).

Plant material

The Minnesota genotypes Bert, MN1301, MN0901, MN0301, Lambert, Granite, MN1801, MN1401, A3237 and MN1402 were used. Seeds of the desired genotype were sterilized by positioning the seeds in a single layer on the bottom of a 15×100 mm petri dish. Three petri dishes containing seeds were placed uncovered into a glass desiccator with a 250 ml beaker containing 100 ml Chlorox™ (Di et al., 1996). Three and a half ml of 12N HCl were carefully added to the chlorox to create chlorine gas and the lid fitted tightly. The seeds were exposed to the fumes for approximately 24 hours before removing from the chamber.

In a sterile flow hood, 15 healthy seeds were placed on 16 petri plates (25×100 mm) with germination media (GM) containing B5 salts and vitamins (Gamborg et al., 1965), MSIII iron stock (Murashige and Skoog, 1962), 2% sucrose, 0.8% agar (Purified Agar, BBL®; Becton Dickinson; pH 5.8). About 3 plates were stacked together, wrapped in clear bags with air holes, and incubated in a room fluctuating between 18–30° C. under 18 hours light/6 hours dark (90–150 $\mu E/m^{-2}s^{-1}$) for 5–7 days, or until the cotyledons turned green but before the first leaves grew out of the cotyledon.

Preparation of Agrobacterium

Working glycerol stocks of Agrobacterium strains AGL1 and LBA4404 were prepared by first streaking a permanent glycerol stock of the appropriate strain onto YEP agar-solidified plates (10 g/l peptone, 5 g/l NaCl, 5 g/l yeast extract, 1.5% agar; pH 7.0) containing the appropriate antibiotics. For strain AGL1, 5 mg/l rifampicin and 5 mg/l tetracycline were added and 50 mg/l hygromycin was added for strain LBA4404. The plates were incubated at 25° C. for 2 days or until individual colonies grew. At this time, a single colony was removed and placed into 50–200 ml liquid YEP media containing the appropriate antibiotics above. The cultures were allowed to shake at 25° C. for approximately 2 days. After saturation was reached, 9 ml of sterile 50% glycerol was added to 21 ml of the liquid culture and stored at −70° C. in 1 ml aliquots.

On the day before explant inoculation, 3 ml of the working glycerol stock or the YEP culture were added to two flasks with 200 ml YEP media amended with the appropriate antibiotics. The cultures were grown at 25° C. and shaken for 20 hours (until the $OD_{650}$ reached 1.0). Before inoculation, 50 ml aliquots of the liquid culture were placed into Falcon® tubes and centrifuged for 10 minutes at 4,500 rpm at 20° C. to pellet the cells. The supernatants were removed and the pellets were resuspended in 25 ml liquid co-culture media containing 1/10 B5 salts, MSIII iron stock, 3% sucrose, 20 mM 2-[N-morpholino]ethanesulfonic acid (MES) (pH5.4) and filter-sterilized B5 vitamin, 200 µM acetosyringone, 1.67 mg/l 6-benzyl-aminopurine (BAP), and 0.25 mg/l gibberellic acid (GA3). The final cell density was around an $OD_{650}$ of 1.8–2.0.

Explant Inoculations and Co-culturing

In several experiments, half of the plates with the seedlings were placed at 4° C. for about 24 hours prior to inoculation. The remaining plates in these experiments and all other experiments did not undergo this cold-treatment. Plates with contaminated seedlings were discarded and the remaining used for wounding and infection. For every 50 ml co-culture suspension, 30 seedlings were set aside to dissect at a time, totaling about 50 explants per treatment. Only seedlings that were green and free of damage were selected for dissection.

For each seedling, the roots and the majority of the hypocotyl were removed approximately 3–5 mm below the cotyledonary node by cutting the hypocotyl with a scalpel (Hinchee et al., 1998). The two cotyledons were then separated by cutting vertically through the hypocotyl region resulting in two explants. The epicotyl was subsequently removed on both explants, including all primary leaves and shoot meristems, and both the axillary bud and cotyledonary node were wounded by cutting about 10 times with a scalpel blade perpendicular to the hypocotyl. After all explants in a set were wounded (about 50), they were placed in a 25×100 mm petri plate containing 50 ml co-culture suspension for 30 minutes or inoculated into the 25 ml co-cultivation/Agrobacterium suspension for 30 minutes. The explants were then cultured on an agar-solidified co-culture media (0.5%) either without the addition of a test agent (e.g., cysteine) in 15×100 mm petri plates on top a sterile Whatman®#1 filter paper; five explants per plate with adaxial side down. Five plates were stacked together and wrapped in Parafilm®M then incubated at either 22° C. or 25° C. for 5 days in the dark.

Selection and Regeneration

After 5 days, the explants were washed in a liquid shoot induction media (B5 salts, MSIII iron stock, 3% sucrose, 3 mM MES, and filter sterilized B5 vitamins, 1.67 mg/l BAP, 100 mg/l cefotaxime, and 500 mg/l ticarcillin; pH 5.6) to remove excess Agrobacterium. Seven to ten explants from each cysteine level were washed in liquid shoot induction medium and placed in GUS histochemical stain (Jefferson et al., 1987). These explants were scored for GUS transient expression. Five to ten explants from each group were imbedded into a single 25×100 mm petri plate with solid shoot induction media (0.8% agar and agent, e.g., 400 mg/l cysteine) containing PPT concentrations of 1.33 mg/l, 3.33 mg/l, or 5.0 mg/l for selection. The plates were then incubated in a growth chamber with a fluctuating temperature between 18° C-30° C. under a 18 hours light/6 hours dark cycle at 90–150 $\mu E/m^{-2}s$.

The explants were removed from the chamber after 14 days and transferred to fresh shoot induction media containing herbicide selection. During the transfer, the hypocotyl was carefully removed from the developing shoot mass and imbedded into the media with the differentiating tissue flush with the media surface. The plates were placed back into the growth chamber for an additional 2 weeks. At the 4 week time point, explants without de novo shoot production were discarded. The cotyledons were then removed from the differentiating tissue by cutting at the base of the node and the callus trimmed before transferring into shoot elongation media containing MS salts (murashige and Skoog, 1962), MSIII iron stock, 3% sucrose, 3 mM MES, 0.8% agar, and filter sterilized B5 vitamins, 50 mg/l asparagine, 100 mg/l pyroglutamic acid, 1 mg/l zeatin riboside, 0.1 mg/l indoleacetic acid, 0.5 mg/l $GA_3$, 100 mg/l cefotaxime, 500 mg/l ticarcillin, 1.3–5 mg/l PPT; pH 5.6). Also at this time, a percentage of the explants were sliced into about 10 sections and stained for both GUS positive sectors and GUS positive shoots. Every 2 weeks the explants were transferred into new shoot elongation media after removing dead plant tissue and the bottom of the explant cut to encourage shoot elongation of transformed shoots.

Experimental Design

Experiments #1, #2, and #3 were to determine whether cysteine had an effect on Agrobacterium infection and/or transgenic shoot production and, if so, at what concentrations. Five levels of cysteine were tested: 0 mg/l, 100 mg/l, 200 mg/l, 300 mg/l, and 400 mg/l. Cysteine was incorporated into the solid co-culture media by preparing the media as described hereinabove and dissolving the L-cysteine into the filter sterilized components. For these three experiments, no cysteine was added into the liquid co-cultivation media. To reduce experimental error, explants were placed randomly on all five different treatments and all plates within a treatment were shuffled after completion of the experiment. After co-cultivation, the explants in each treatment were placed on shoot induction media with ½ the concentration of cysteine as in the co-cultivation media. The specific details for each experiment are as follows:

1. Experiment #1 used the Minnesota genotype Bert and Agrobacterium strain AGL1 containing the BSF16 binary plasmid. A total of 276 explants were wounded and infected with Agrobacterium. After co-cultivation, 10 explants of each treatment were immersed into GUS stain and assayed for transient expression and the remaining explants were washed and transferred to shoot induction media containing 1.33 mg/l PPT for all four weeks. De novo shoots were produced on 74% of the treatments containing 0 mg/l cysteine, 57% on 100 mg/l, 63% on 200 mg/l, 70% on 300 mg/l, and 77% on 400 mg/l at four weeks. Of those explants with differentiating tissue, fifteen were dissected and sacrificed to GUS stain and the remaining were transferred to shoot elongation media containing 3.33 mg/l PPT.
2. Experiment #2 used the Minnesota genotype MN1301 and Agrobacterium strain AGL1 containing the BSF16 binary plasmid. A total of 229 explants were dissected, cut, and inoculated. For each cysteine-treatment, half of the explants were incubated during co-cultivation at 21–22° C. and the other half at 25° C. Five explants of each cysteine/temperature treatment were sacrificed to GUS stain and the remaining transferred to fresh shoot induction media containing 1.33 mg/l PPT for 2 weeks. The herbicide level was raised to 3.33 mg/l PPT for the second 2 weeks on shoot induction media. Because of poor de novo shoot growth (35% on 0 mg/l cysteine, 22.8% on 100 mg/l, 32% on 200 mg/l, 42% on 300 mg/l, and 28% on 400 mg/l) and contamination, all explants were sacrificed to GUS stain at the 4 week time point.
3. Experiment #3 used the Minnesota genotype MN0901 and Agrobacterium strain AGL1 containing the BSF16 binary plasmid. Seedlings were germinated as usual, however, one half of the plates were placed at 4° C. for 24 hours before inoculation. A total of 390 explants were wounded and inoculated. For each cysteine/seedling-temperature treatment, one half of the explants were incubated during co-cultivation at 21–22° C. and the other half at 25° C. After co-cultivation, 5 explants of each treatment (seedling-temperature/cysteine/incubation-temperature) were sacrificed to GUS stain and the remaining transferred to fresh shoot induction media containing 1.33 mg/l PPT for the first 2 weeks. The herbicide level was increased to 3.33 mg/l PPT for the second 2 weeks of shoot induction media. Of those explants developing de novo shoots (64% on 0 mg/l cysteine, 53% on 100 mg/l, 54% on 200 mg/l, 53% on 300 mg/l, and 61% on 400 mg/l), four of each treatment were dissected and sacrificed to GUS stain. The remaining explants were transferred to shoot elongation media containing 3.33 mg/l PPT.

Experiments #4, #5, and #6 were designed to determine whether cysteine is beneficial in the liquid co-cultivation media as well as the solid media, whether a higher selection level of 5 mg/l PPT in the shoot induction media increases selection for transgenic shoots, and whether cysteine can improve Agrobacteria infection in those genotypes known to respond poorly to the cotyledonary-node method. The 2 levels of cysteine used in both the liquid and solid co-cultivation media were 400 mg/l (the optimal cysteine level found in the previous 3 experiments) and 0 mg/l as a control. L-cysteine was incorporated into both the liquid and solid co-cultivation media by dissolving into the B5 vitamin solution and filter sterilizing before adding to the media. Therefore, the 4 treatments in the three experiments were 0 (mg/l cysteine) liquid (L), 0 (mg/l cysteine) solid (S); 400L,0S; 0L,400S; and 400L,400S. After the 30 minute incubation in liquid co-cultivation media, the explants were placed randomly between the 2 different solid media and the plates shuffled within each treatment to reduce experimental error. After co-cultivation, the explants were placed on shoot induction media with ½ the concentration of cysteine as in the solid co-cultivation media. Specific details for each treatment are as follows:

4. Experiment #4 used the Minnesota genotype Bert and Agrobacterium strain AGL1 containing the BSF16 binary plasmid. One day before the inoculation, one half of the seedlings were placed at 4° C. while the other half remained in the chamber fluctuating from 18–30° C. A total of 318 explants were wounded and inoculated. The explants were incubated at 25° C. for 5 days in the co-culture media. After co-cultivation, 7 explants of each cysteine/seedling temperature treatment were sacrificed to GUS stain for transient expression. For the remaining explants of each treatment, one half of the explants were placed in shoot induction media containing 3.33 mg/l PPT and the other half in shoot induction media containing 5 mg/l PPT. The same PPT concentration was used throughout the entire 4 weeks in shoot induction media. Of those explants that developed de novo shoots (76% on 0L,0S; 47% on 400L,0S; 75% on 0S,400L; and 68% on 400L, 400S), 3 explants of each treatment (cysteine/seedling temperature/PPT concentration) were cut and sacrificed to GUS stain. The remaining explants were placed into shoot elongation media containing 3.33 mg/l PPT.
5. Experiment #5 used the Minnesota genotypes MN0901, Granite, and MN1401 and Agrobacterium strain AGL1 containing the BSF16 binary plasmid. A total of 267 explants of the genotype MN0901, 59 explants of the genotype Granite, and 74 explants of the genotype MN1401 were wounded and inoculated. After co-cultivation, 10 explants of each cysteine treatment were sacrificed to GUS stain for transient expression. The remaining explants were placed equally between shoot induction media containing either 3.33 mg/l PPT or 5 mg/l PPT. The herbicide concentration was not changed during the four week period on shoot induction media.
6. Experiment #6 used the Minnesota genotype MN1301 and Agrobacteria strain AGL1 containing the BSF16 binary plasmid. A total of 309 explants were wounded and inoculated. Ten explants of each cysteine level were sacrificed to GUS stain for transient expression, and the remaining explants placed equally among shoot induction media containing either 3.33 mg/l PPT or 5 mg/l PPT. The concentration of PPT remained the same throughout the four weeks in shoot induction media.

To determine whether 400 mg/l was the optimal concentration of cysteine (Experiment #7), the Minnesota genotype Bert and Agrobacterium strain AGL1 containing the BSF16 binary plasmid were used. For this particular experiment, the following five concentrations of cysteine were used: 0 mg/l, 400 mg/l, 600 mg/l, 800 mg/l, and 1 g/l. The 5 concentrations of cysteine were added into the solid co-cultivation media through filter sterilization as mentioned above. No cysteine was added into the liquid media. A total of 223 explants were wounded-and inoculated. Explants were placed randomly on co-cultivation plates with all 5 treatments and the plates shuffled within each treatment to reduce experimental error. After 5 days of incubating at 25° C., 10 explants of each cysteine treatment were sacrificed to GUS stain and the remaining explants were imbedded in shoot induction media containing either 3.33 mg/l PPT or 5 mg/l PPT. For those treatments that contained cysteine, 200 mg/l cysteine was also added to the shoot induction media.

Experiment #8 was designed to determine whether other genotypes respond favorably to Agrobacterium infection when exposed to cysteine during co-cultivation, whether an increase in infection occurs using other Agrobacteria strains and binary plasmids, and whether there is an interaction between cysteine and the explant without Agrobacterium present. The Minnesota genotypes MN090 1, MN1801, MN0301, and Lambert were used along with two Agrobacterium strains, AGL1 and LBA4404. Cysteine was added to the liquid co-cultivation media at the concentration of 400 mg/l for all treatments, however, the solid media contained either 0 mg/l or 400 mg/l cysteine. A total of 153 explants of the genotype MN0901 were wounded and infected: 105 were infected with the LBA4404 Agrobacterium strain, 36 were infected with the AGL1 Agrobacterium strain, and the remaining 12 were uninfected. The Agrobacterium strain AGL1 was the only strain used to infect the other three genotypes, MN1801 (74 explants), MN0301 (52 explants), and Lambert (85 explants). Explants were placed randomly on plates containing either 0 mg/l or 400 mg/l cysteine and shuffled to reduce experimental error. After 5 days, between 5–12 explants of each treatment were sacrificed to GUS stain for transient expression. The remaining explants infected with the strain AGL1 were then imbedded into shoot induction media containing the appropriate concentration of cysteine (either 0 mg/l or 400 mg/l) and split equally between 3.33 mg/l PPT or 5 mg/l PPT. Those explants infected with LBA4404 were discarded after co-cultivation.

Experiment #9 was designed to address whether other sulfur-containing compounds improve Agrobacterium infection, and whether an increase in infection occurs using other Agrobacteria strains and binary plasmids. The Minnesota genotype MN0901 was used with the two Agrobacteria strains, AGL1 and LBA4404. Four different co-cultivation media were made by filter sterilizing in one of the following components: 400 mg/l glutathione, 400 mg/l methionine, 400 mg/l cysteine, or normal co-culture media. A total of 321 explants were wounded and inoculated. Agrobacterium strain AGL1 was used to infect 183 of the explants while the remaining 138 were infected by the strain LBA4404. Explants were randomly distributed among the 4 different treatments and the plates shuffled within a treatment to reduce the experimental error. One half of the explants were incubated for 5 days at 22° C. and the other half at 25° C. After co-cultivation, 5 explants of each treatment (media type/incubation temperature/Agrobacteria strain) were sacrificed to GUS stain for transient expression. Only those explants that were infected with AGL1 were placed in shoot induction media containing 3.33 mg/l PPT for 4 weeks. Those explants infected with LBA4404 were discarded after co-cultivation.

Scoring of GUS positive sectors

The level of infection was scored using the GUS gene as a phenotypic marker immediately after co-culture and again after 4 weeks in shoot induction media. As it can be difficult to score the explants after co-cultivation due to the variation among explants and, in some cases, a complete staining of the target tissues, 6 categories were formed to assess the success of infection:

4) None=There were no GUS positive sectors on any of the explants;
5) Very low=Not all explants have GUS positive sectors, however, some have discrete foci usually seen on the hypocotyl or cot-node region.
6) Low=More than ¾ the explants have GUS positive sectors in discrete foci on the hypocotyl and the cot-node region, but the foci are not numerous (<20).
7) Medium=More than ½ the explants have significant GUS positive sectors at the cot-node region and hypocotyl, some seen as long lines of cells or larger sectors.
8) Good=More than ¾ the explants have significant staining at the hypocotyl, the entire cot-node region, and on the cotyledons. Some areas have no distinct foci but complete staining of the tissue.
9) Superior=All explants have significant staining at the hypocotyl, cot-node region, and the cotyledons. Almost all explants have regions that are completely GUS positive.

To reduce bias, samples were chosen at random and the level of infection scored before noting the treatment conditions. Samples that were between two categories are marked accordingly; those samples that resembled one category more than another were marked with a capital "X" and the other with a lowercase "x".

For the 4 week data, the minimum number of transformation events was recorded. Those explants with a GUS positive sector in the differentiating tissue giving rise to shoots were recorded with the number of transformation events in bold and italicized (FIGS. 2–5). Shoot data was obtained by recording the number of fully formed shoots seen on an explant.

Results

One major limitation in the Agrobacterium-based cot-node method is the inefficiency of DNA transfer from Agrobacterium to the target plant tissue, which is likely due to a strong defense system present in soybean. Various antioxidants have been used in other plant systems to try and counteract the defense response to wounding and infection, however, these experiments were not always successful.

Data from transient expression after co-cultivation in experiments #1, #2 and #3 show a significant increase in GUS expression in those cultures containing cysteine compared to those without (FIG. 1C). With all three Minnesota genotypes (MN1301, MN0901, and Bert), the trend is for a higher level of infection as the concentration of cysteine is increased from 100 mg/l to 400 mg/l. The subtreatments involving changes in temperature 24 hours before inoculation (4° C. vs. 28° C.) and incubation during co-cultivation (22° C. vs. 25° C.) do not seem have significant effects on Agrobacterium infection. Overall, the explants incubated without cysteine had low levels of GUS positive foci while those with cysteine, especially those containing 300 and 400 mg/l, had extensive GUS positive sectors. Since the highest concentration of cysteine showed the most infection, another experiment (#7) was conducted to determine if higher levels of cysteine, i.e., 600, 800, or 1000 mg/l, was beneficial (FIG. 1C). Although all 4 concentrations resulted in similar levels of infection, there was little to no growth of the hypocotyls in explants co-cultivated in 800 and 1000 mg/l cysteine.

In one control experiment, explants were wounded but not infected with Agrobacterium and placed on 400 mg/l co-cultivation media (FIG. 1C, experiment #8). In a second experiment, the explants were wounded, infected, and immediately placed into GUS stain containing 400 mg/l cysteine. There was absolutely no GUS positive sectors on any explant, suggesting the stained regions are not due to an interaction between cysteine and the GUS stain.

The AGL1 strain contains the binary plasmid BSF16 with a gene that encodes for a protein rich in cysteine and methionine. Experiments #8 and #9 (FIG. 1C) clearly show that those explants infected with the LBA4404 strain containing the binary plasmid pTOK233 and exposed to cysteine during co-cultivation exceed in the frequency of GUS positive sectors over the control explants. In fact, the explants exposed to LBA4404 are slightly more infected than those exposed to BSF16.

A greater infection of the cot-node region after co-cultivation does not necessarily mean that there will be an increase in GUS positive sectors 4 weeks later. To date, a sample from the first 4 experiments has been sacrificed to GUS stain and scored for GUS positive sectors (FIGS. 2, 3, 4, and 5). As summarized in FIG. 1C, explants exposed to cysteine during co-cultivation have an increased number of GUS positive sectors. Control explants at 0 mg/l range in the 4 experiments between an average of 1.9 GUS positive sectors/explant to 5.9 GUS positive sectors/explant while the range of 400 mg/l is an average of 14.1 GUS positive sectors/explant to 18.1 GUS positive sectors/explant. Therefore, the greater infection rate seen after co-cultivation leads to more GUS positive sectors after 4 weeks on PPT selection.

Figure 7:
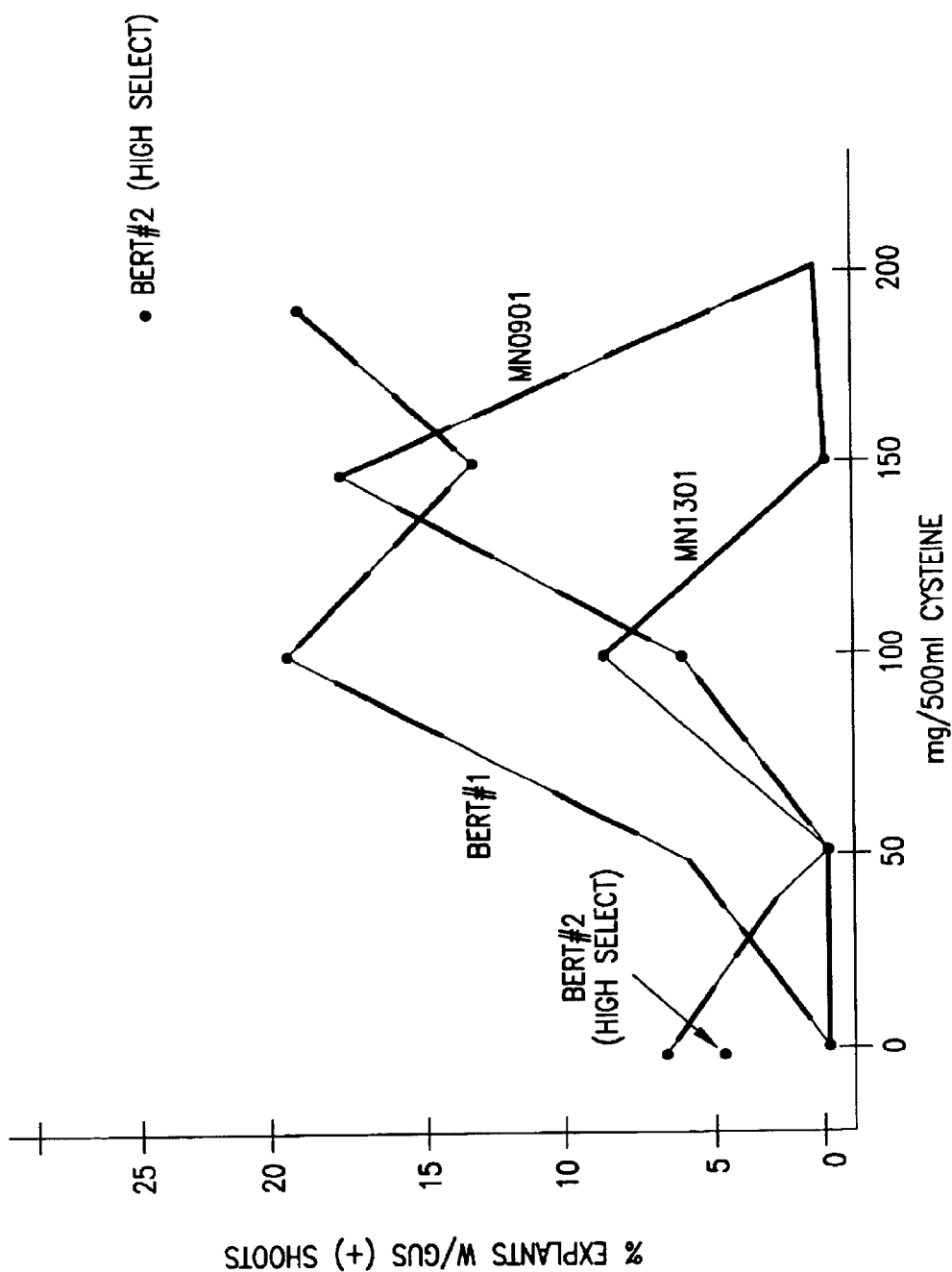
FIG. 7 is a graph of the number of GUS$^+$ shoots per concentration of L-cysteine for various genotypes.
Figure 8:
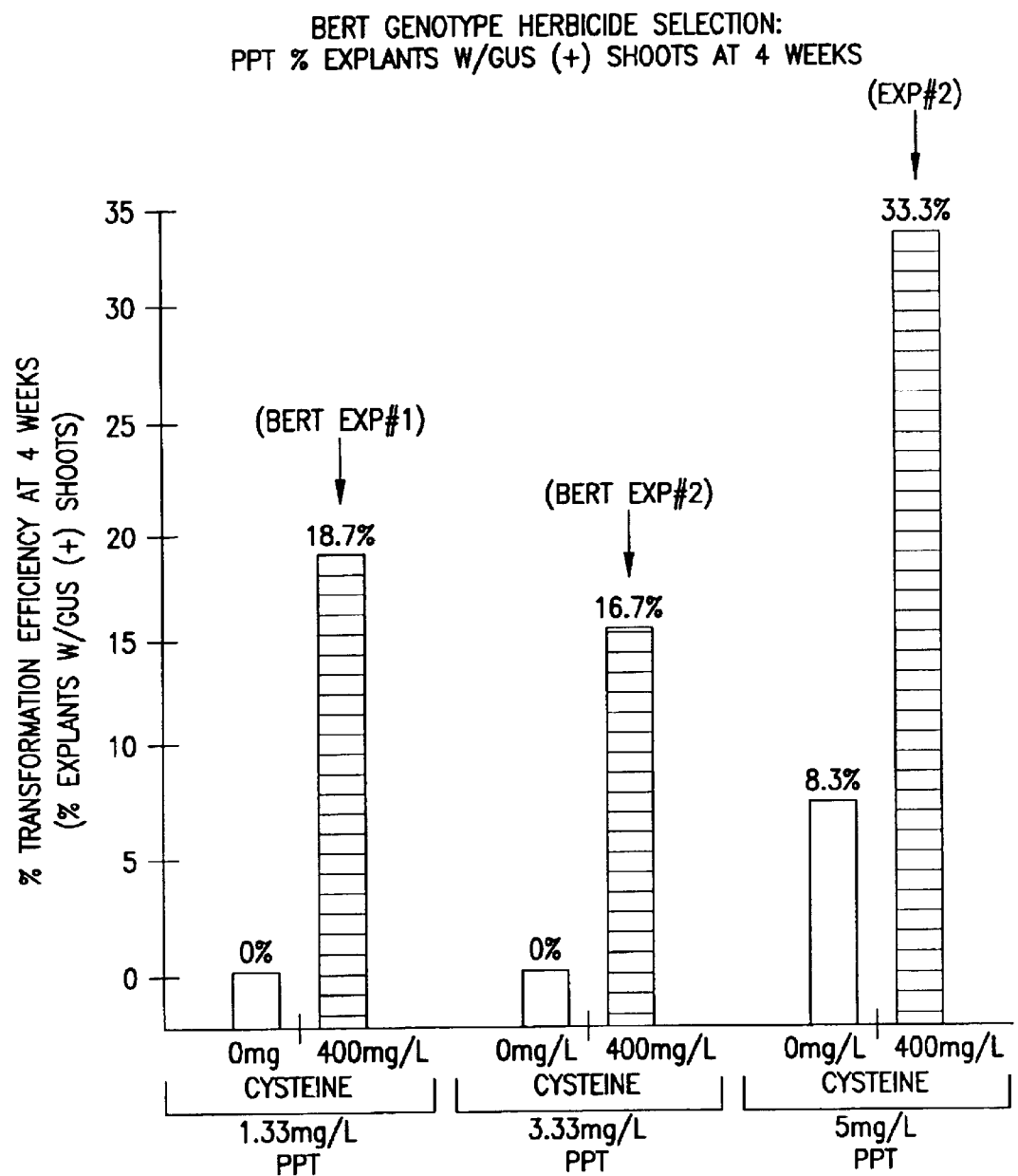
FIG. 8 is a graph of the percent of explants with GUS$^+$ shoots per concentration of L-cysteine and PPT.

The shoot data accumulated for experiments #1-#3 were plotted (FIG. 7). There was not a steady progression in shoot formation as the concentration increases in these experiments. The raw data (FIGS. 2, 3, and 4) show that although shoots may not be formed, there are sectors of GUS positive tissue that lie on the differential tissue giving rise to shoots. Because these experiments underwent a low selection pressure (3.33 mg/l or 5 mg/l PPT) during shoot induction, increasing the selection pressure may increase the number of transgenic shoots. Explants in experiment #4 were co-cultivated in either 400 mg/l cysteine or 0 mg/l cysteine and subsequently embedded into shoot induction media containing either 3.33 mg/l PPT or 5 mg/l PPT. The data show that for the genotype Bert, there is an increase in the percent explants with a GUS positive shoot at 0 mg/l cysteine from 0%–8.3% when the selection is increased (FIGS. 5 and 8). However, the most drastic increase is seen with those explants that were incubated in 400 mg/l cysteine, from 16.7% to 33.3%. These results suggest that increased infection obtained by supplementing the co-cultivation media with cysteine may give rise to a higher percentage of shoots under appropriate selection conditions.

Cysteine was added to the liquid media in experiments #4, #5 and #6 to determine whether the interaction occurs right after inoculation or during the five day co-cultivation period. The experiments were set up by adding either 0 mg/l or 400 mg/l cysteine to both the solid and liquid co-culture media resulting in 4 different treatments. Data from explants stained after co-cultivation show that only those explants that have been exposed to the cysteine in the solid media result in increased infection (FIG. 1C).

To determine whether the sulfur group in cysteine is a factor in increasing Agrobacterium infection, methionine, glutathione, or cysteine was added to the co-cultivation media and data collected after co-cultivation (FIG. 1C, experiment #9). Although explants exposed to glutathione and methionine did not result in an increase in infection, the concentration of these and other sulfhydryl-containing agents, such as methionine, glutathione and DTT, effective to enhance Agrobacterium transformation, may be different than those tested (see Example II). Therefore, it is envisioned that other sulfhydryl-containing agents can be employed in the methods of the invention.

The response of soybean to the cot-node method is genotype dependent: the majority of genotypes respond poorly to either Agrobacterium infection or to the tissue culture process itself. Minnesota genotypes that respond poorly to the cot-node method (MN1401, Granite, Lambert, MN1801, and MN0301) were incubated during co-cultivation with cysteine (400 mg/l) included in the co-cultivation media (FIG. 1C; experiments #5 and #8). Although these genotypes did not result in the same level of infection as the genotype MN0901 when exposed to 400 mg/l cysteine, there was a significant increase in infection over the explants that did not undergo the cysteine treatment, especially the genotypes MN 1801 and Granite. These results suggest that the cysteine treatment may increase the number of genotypes amenable to the cot-node method.

EXAMPLE II

Figure 1I:
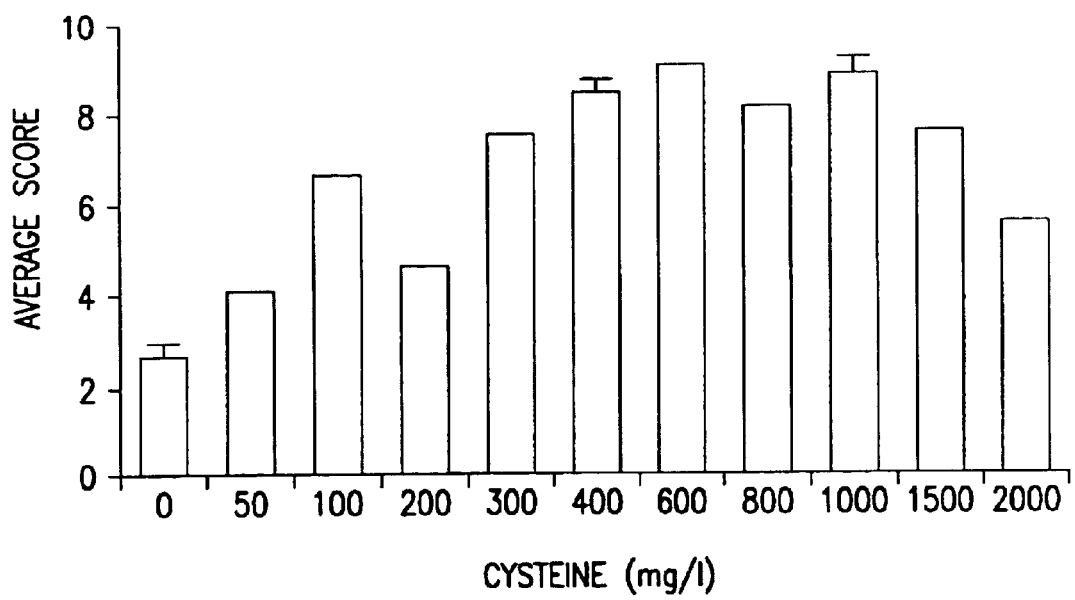
Figure 6:
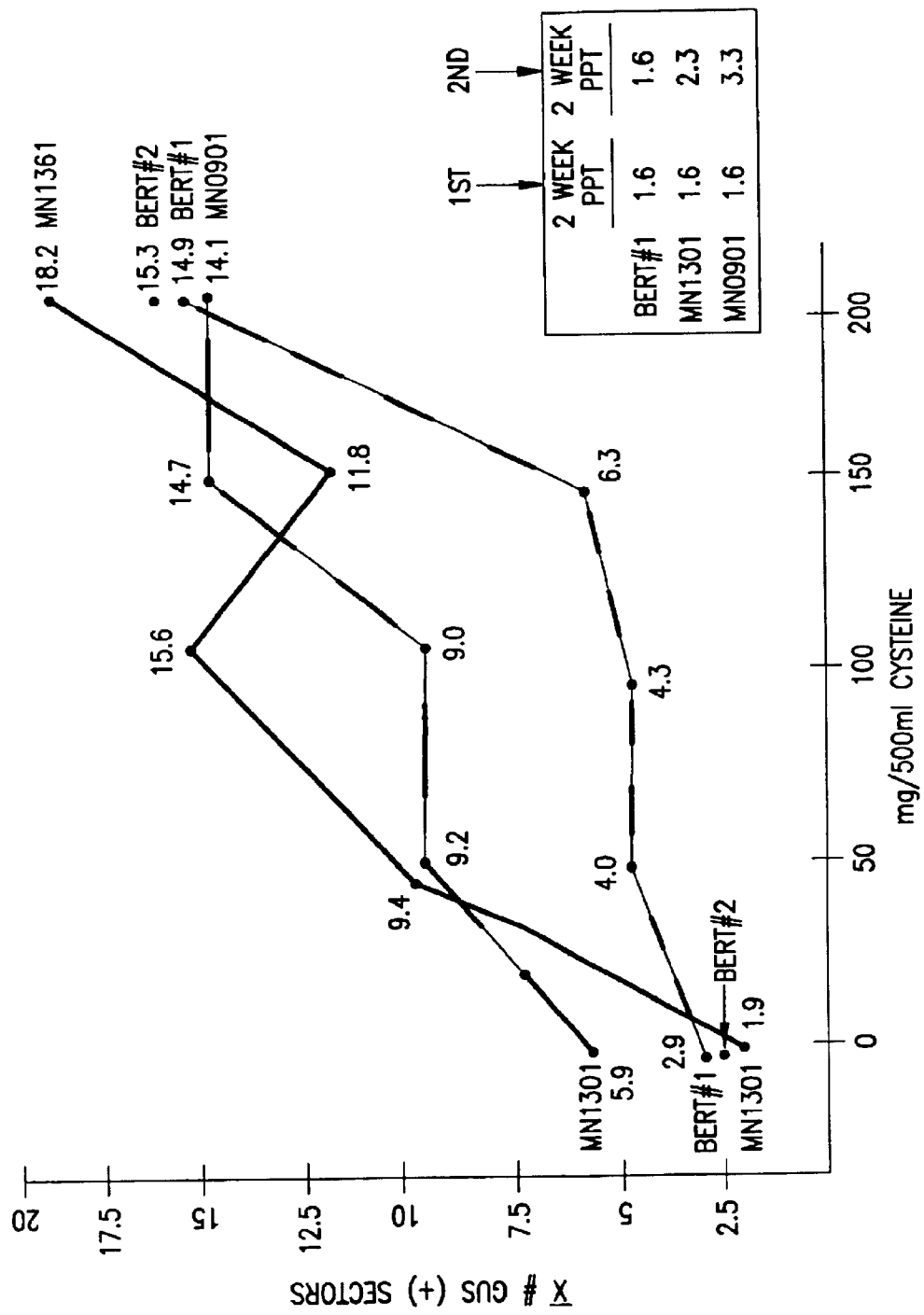
FIG. 6 is a graph of the number of GUS$^+$ sectors per concentration of L-cysteine for various genotypes.

The following results include results from experiments described in Example I as well as results from additional experiments. Wounded soybean cot-node explants prepared from the cultivar 'Bert' were co-cultivated with Agrobacterium on solid co-cultivation medium containing various levels of cysteine for 5 days. Agrobacterium strain AGL1 was employed which contains the binary plasmid, pBSF16, which carries in its T-DNA the bar gene as a selectable marker and the *E. coli* gusA (GUS) gene under control of the CaMV 35S promoter; gusA expression occurs in plant cells but not in bacteria due to an altered 5' leader sequence (Molvig et al., 1997). Following co-cultivation, T-DNA transfer to cells in the soybean cot-node was determined by scoring GUS transient expression ($GUS^+$) using GUS histochemical staining (FIG. 1A1). For these experiments, GUS staining was scored in the cot-node region, defined as the node tissue between the junction of the epicotyl and hypocotyl, and the cotyledon, because these cells proliferate to form plant-regenerating tissues. The mean frequency of explants that contained at least a single focus of GUS staining cells ($GUS^+$ focus) in the cot-node region across experiments was determined for each level of cysteine tested in eight replicates of the transient Agrobacterium-infection assay. Adding cysteine to the solid co-cultivation medium increased the average frequency of explants containing a $GUS^+$ focus at the cot-node from only 30% for explants on medium containing no cysteine to nearly 100% in the treatments ranging from 300 to 1000 mg/l cysteine (FIG. 1D). The physical appearance of the explants cultured in cysteine also was improved; specifically, there was less browning on the cut and damaged surfaces of the hypocotyl, cot-node region, and the cotyledon of the explants (FIG. 1B).

The most striking feature of these 5 day explants was the increased numbers of $GUS^+$ cells observed on explants co-cultured in cysteine compared to explants co-cultured without cysteine (FIG. 1B). Scores were thereby assigned that ranged from 0–10; 0 for no GUS staining on any explant and 10 for all explants exhibiting extensive staining on the cot-node region, hypocotyls, and cotyledons, including areas of complete staining (FIG. 1D). From this ranking system, the explants co-cultivated in the absence of cysteine had an average score of 2.6 whereas explants co-cultivated in concentrations from 400 mg/l to 1000 mg/l cysteine scored between 8 and 9. Therefore, addition of cysteine to the co-cultivation medium resulted in an increase in T-DNA delivery frequency when expressed per explant and as a function of the numbers of $GUS^+$ cells per explant.

Cysteine Increases Stable Transformation.

Figure 9:
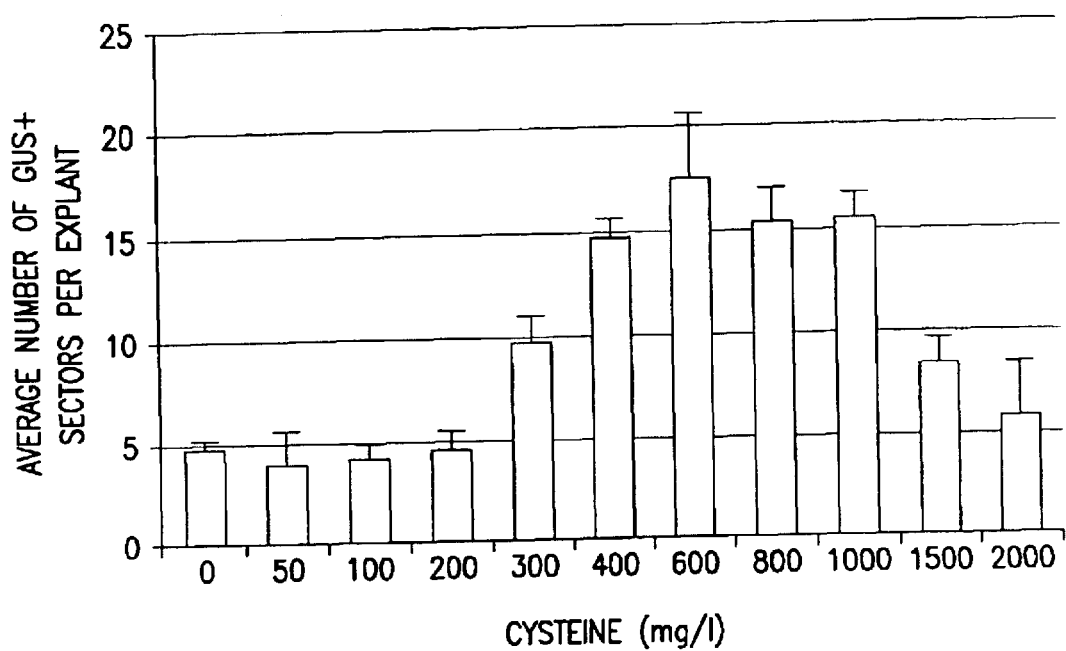
FIG. 9 is a comparison of GUS expression on explants co-cultivated on different cysteine treatments after 28 days on shoot initiation medium supplemented with PPT. The average number of GUS$^+$ sectors per explant was calculated for the 11 different cysteine concentrations across 7 independent experiments. GUS$^+$ sectors were counted only when clonal sectors were identified; therefore, these averages under-represent the number of actual Agrobacterium infections on an explant. Standard error between experiments is represented by [τ] above each cysteine treatment. The cysteine treatments 300–1000 mg/l and 1500 mg/l significantly differ from 0 mg/l cysteine at α=0.05 (P≦0.001 and 0.05≧P>0.01, respectively).

To determine the effect of adding cysteine to the co-cultivation medium on stable transformation, co-cultured explants were cultured for 28 days on a shoot-inducing medium containing the herbicide, phosphinothricin (PPT). During the 28 day incubation, the explants usually form de novo callus and shoots in the cot-node region in a structure referred to as a callus/shoot pad (FIG. 9). The callus/shoot pads were sliced in approximately 5 mm sections, immersed into GUS histochemical stain, and scored for $GUS^+$ sectors throughout the callus/shoot pad. Those $GUS^+$ sectors that did not divide significantly (e.g., sectors that appeared as small clusters of cells) were not counted; therefore, $GUS^+$ sector determinations represented a minimum number of T-DNA integration events. The average number of $GUS^+$ sectors per explant was significantly higher ($P<0.05$) in the cysteine treatments ranging from 300 to 1000 mg/l compared to the no cysteine control (FIG. 9) and there was greater than a 3-fold increase in $GUS^+$ sectors on explants co-cultivated with 400 to 1000 mg/l cysteine over the no cysteine control. Although the explants that were co-cultivated in 1000 mg/l cysteine had little callus growth on the hypocotyl, a healthy callus/shoot pad grew from the explant with a 3.6-fold increase in $GUS^+$ sectors over the control explants.

Figures 10A, 10B:
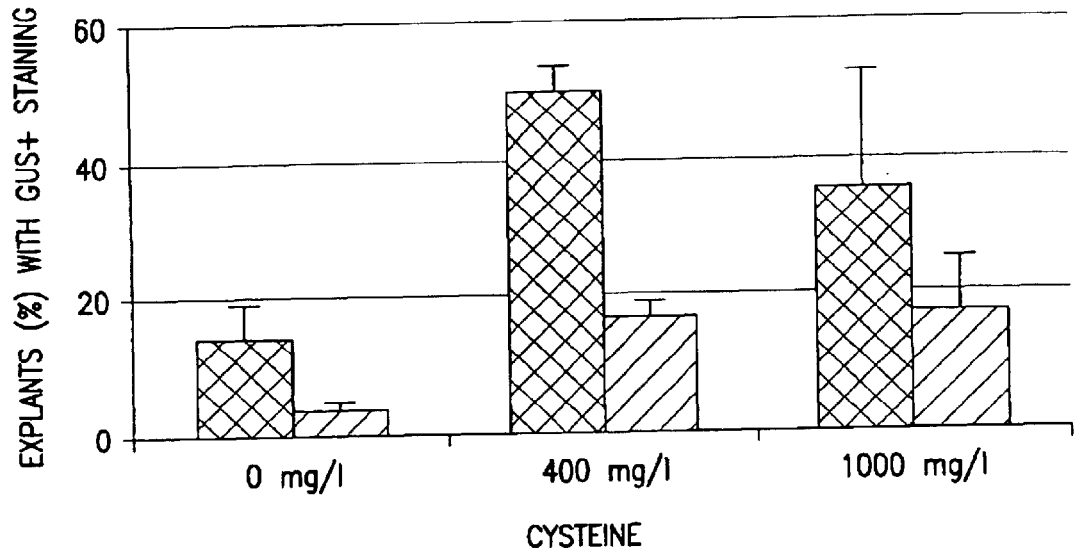
FIG. 10 is the average percent of explants with either GUS$^+$ shoot primordia (■) or differentiated sectors (■) after 28 days on shoot induction medium supplemented with PPT compared between various cysteine treatments. (A) shows the average percent was calculated for 0 mg/l cysteine®=9, n=88), 400 mg/l cysteine®=8, n=105), and 1000 mg/l cysteine®=4, n=34) experiments. Only those explants containing GUS$^+$staining in shoot primordia with obvious trichomes were scored as positive as well as those sectors at the base of developing shoots (referred to as differentiated tissue sectors). Standard error between experiments is represented by [τ] above each cysteine treatment. Both 400 mg/l shoot primordia and differentiated sectors and 1000 mg/l shoot primordia significantly differ from 0 mg/l cysteine at α=0.05 (P≦0.001 and 0.05≧P>0.01, respectively). (B) The number of explants with shoot primordia from total explants are given according to all cysteine treatments scored.

The formation of transgenic shoot primordia and sectors extending into developing shoot tissues were also scored on 28 day sections of explants co-cultivated on 0 and 400 mg/l cysteine (FIG. 10A). Only those $GUS^+$ shoot primordia with obvious trichomes, which are characteristic to leaf tissue, or $GUS^+$ sectors originating and extending into the tissue at the base of developing shoots (referred to hereafter as differentiating tissue) were scored (FIG. 1A2). The frequency of explants with a $GUS^+$ sector in differentiating tissue was 3.5-fold greater when treated with 400 mg/l than with no cysteine. Even greater was the percent of explants with $GUS^+$ shoot primordia; those explants treated with 400 mg/l cysteine were 5-fold more frequent than those explants not co-cultivated with cysteine. Moreover, all other levels of cysteine tested, except 50 mg/l, resulted in at least one explant with a GUS$^+$ shoot primordia (FIG. 10B). Interestingly, those explants with GUS3$^+$ shoot primordia had single shoots in only 40% of the explants. The other explants possessed multiple GUS$^+$ shoot primordia; in fact, of the 29 explants with multiple shoot masses, 15 had greater than five GUS$^+$ shoot primordia in a cluster with some explants containing up to 25 shoot primordia (FIG. 1A2). Thus, addition of cysteine to the co-cultivation medium increased the proportion of explants exhibiting transgenic shoot primordia and the number of transgenic shoot primordia produced per explant both of which would result from increased Agrobacterium-mediated T-DNA delivery.

Effect of Genotype, Agrobacterium Strain, Binary Plasmid, and Other Factors on Aerobacterium-mediated T-DNA Deliver.

Figure 11:
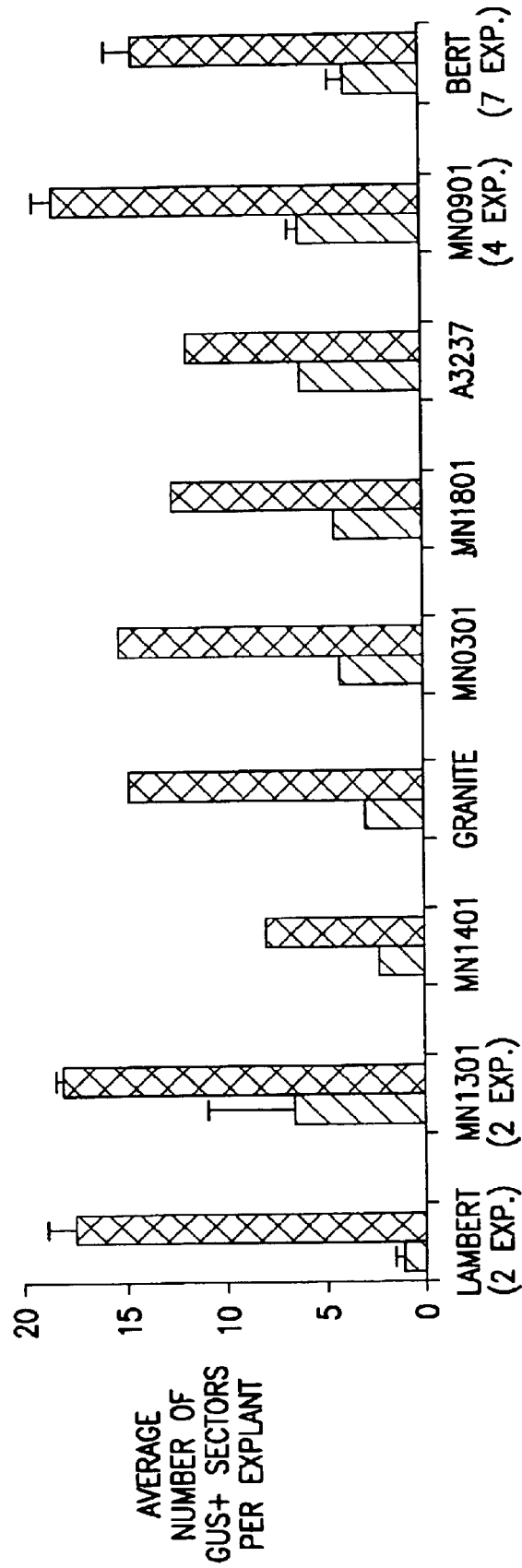
FIG. 11 is the average number of GUS$^+$ sectors per explant of 0 mg/l cysteine ((■) compared to 400 mg/l cysteine (■) across various genotypes after 28 days on shoot induction medium. Clonal GUS$^+$ sectors were scored for nine different genotypes to determine that effects of cysteine on Agrobacterium infection are independent of genotype. Each experiment was performed only once, unless noted. Standard error between experiments is represented by [τ] above each cysteine treatment.
Figure 12A:
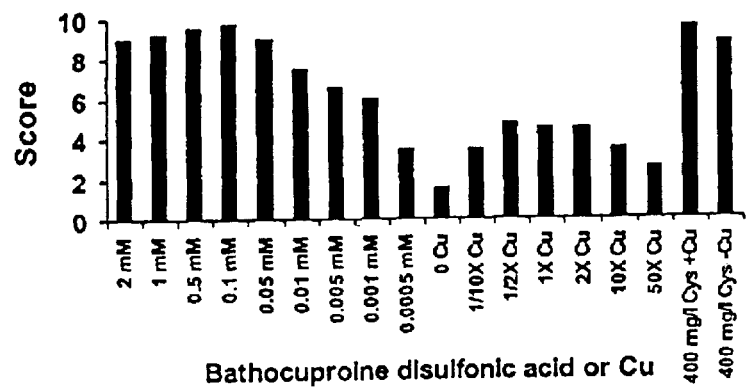
FIG. 12 shows GUS$^+$ results with other exemplary agents of the invention.
Figure 12B:
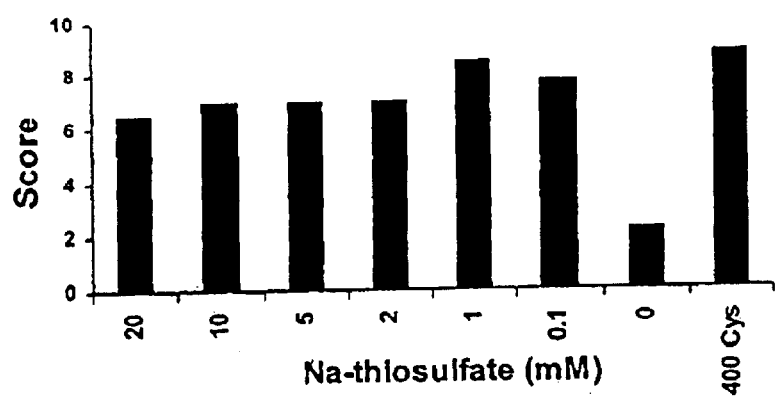
Figure 12C:
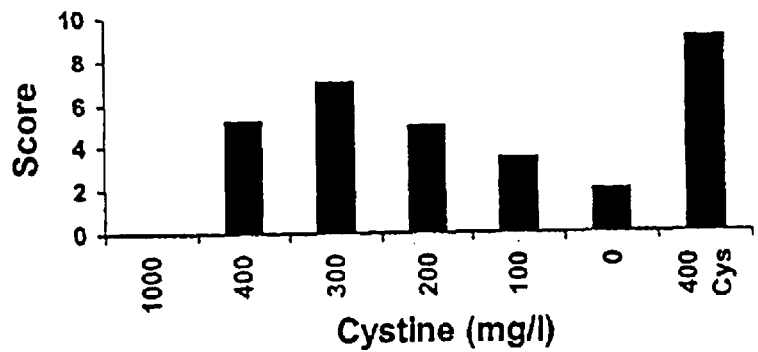
Figure 12D:
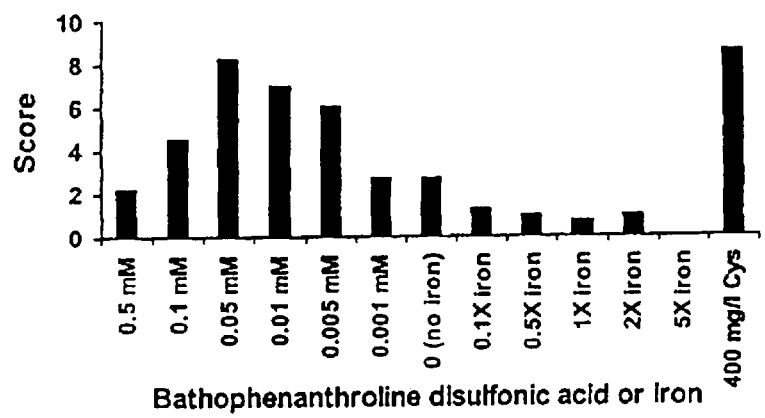
Figure 12E:
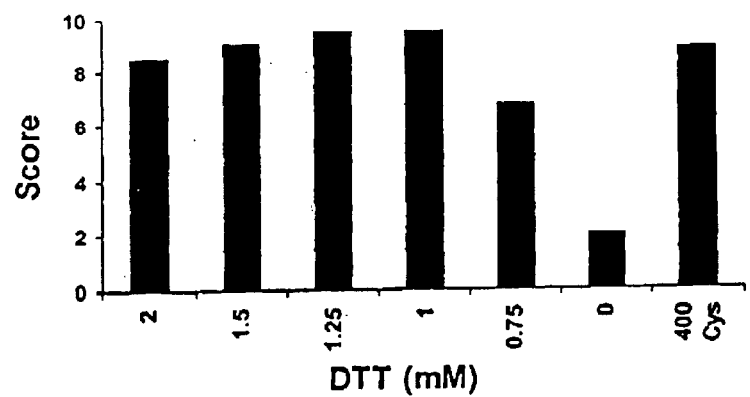
Figure 12F:
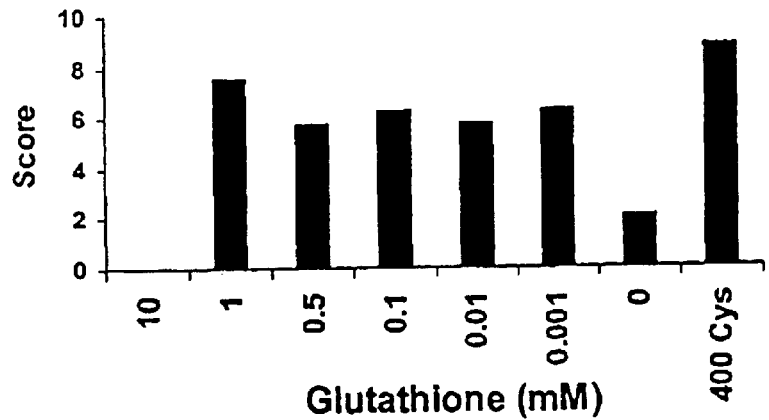

To determine whether the increases in T-DNA delivery and stable transformation at 5 days and 28 days, respectively, were genotype independent or characteristic of Bert only, explants from the genotypes MN0901, A3237, MN1801, MN0301, Granite, MN1401, MN1301, and Lambert were wounded and inoculated. After 5 days in co-cultivation, all genotypes exhibited an increase in frequency of explants with GUS$^+$ foci at the cot-node as well as an increase in the number of foci on a single explant in the cysteine treatments compared to the no cysteine treatment (data not shown). The frequency of GUS$^+$ sectors also was increased at the 28 day time interval, where, for each genotype tested, the average number of GUS$^+$ sectors per cysteine-treated (400 mg/l) explant was significantly greater than the no cysteine treatment (FIG. 11).

A second Agrobacterium strain, LBA4404, carrying the supervirulent binary plasmid, pTOK233 (Hiei et al., 1994), also was tested to determine if the effect of cysteine on Agrobacterium infection was independent of the strain used for transformation. In these experiments, both the frequency of explants with GUS$^+$ foci and the number of foci on an explant at 5 days was greater on explants co-cultivated on cysteine-amended medium compared with explants co-cultivated without cysteine, indicating that the cysteine-dependent increase in T-DNA delivery was Agrobacterium strain independent (data not shown). Co-cultivation temperature has been shown to be an important factor in Agrobacterium infection. Soybean explants were tested for GUS transient expression after co-cultivation in either of two incubation temperatures of 21° C. or 25° C. or a pre-treatment of seedlings at 4° C. 24 hours prior to wounding. Based on the frequency of GUS$^+$ foci on explants at either the 5 day or 28 day time interval, none of these treatments significantly increased Agrobacterium infection (data not shown). The improvement in Agrobacterium-mediated T-DNA delivery involves a general mechanism not limited by soybean genotype, Agrobacterium strain, or binary plasmid.

The effect of cysteine on increasing Agrobacterium-mediated T-DNA delivery into cot-node cells appeared to be exerted on the explant only. Addition of cysteine to either the liquid Agrobacterium culture medium or the medium into which the Agrobacterium were re-suspended for explant inoculation did not increase GUS$^+$ foci on 5 day explants suggesting that cysteine has no direct effect on the capacity of Agrobacterium to infect the explant and transfer its T-DNA. The addition of cysteine to the shoot induction medium for 28 days also did not increase the number of GUS$^+$ sectors on the callus/shoot pad indicating that cysteine was effective only during the co-cultivation step of the transformation procedure. These results suggest that cysteine inhibits wounding and plant pathogen responses, thereby rendering the cot-node cells more susceptible to Agrobacterium infection, which increased the capacity for Agrobacterium-mediated T-DNA delivery into these totipotent soybean cells.

Discussion

Agrobacterium-mediated transformation of soybean offers two primary advantages over methods based on microprojectile bombardment. First, T-DNA integration patterns in plants transformed using Agrobacterium are usually lower in copy number and transgene rearrangements compared to plants transformed using microprojectile bombardment (Pawlowski and Somers, 1996). Simpler transgene integration patterns and lower transgene copy numbers likely increase the probability of producing a transgenic event that does not exhibit unstable transgene expression due to transgene silencing. Thus, there is increasing adoption of Agrobacterium-mediated transformation in both dicot and monocot crops because fewer transgenic events need to be produced. The second reason is that most Agrobacterium-based transformation systems minimize the duration of time explant cells are in tissue culture and often the level of dedifferentiation of the cells targeted for transformation. Long periods of culture are known to increase the frequency of tissue culture-induced genetic variation, or somaclonal variation, including plant sterility and loss of regeneration capacity in tissue cultures (Olhoft and Phillips, 1999). The tissue cultures established for the cot-node method use explants prepared directly from germinated seedlings without significant cellular dedifferentiation, thereby minimizing the likelihood of inducing somaclonal variation (Zhang et al., 1999).

The obvious drawback to the soybean cot-node transformation system is that transgenic plants are produced at lower frequencies compared to Agrobacterium-mediated transformation of other plants (Trick et al., 1997). Factors that are likely limiting to development of an efficient system are 1) the frequency of Agrobacterium-mediated T-DNA transfer into cot-node cells, 2) selection of transgenic cells that retain totipotency, and 3) regeneration of transgenic plants. Therefore, poor Agrobacterium infection ultimately limits the potential successes that can be achieved in improving both selection of transgenic cells and regeneration of transgenic plants. The enzymatic browning observed on the wounded cot-node after Agrobacterium infection can be attributed to activation of both wound and pathogen-defense responses by phenolic oxidation via the coordinated action of polyphenol oxidases (PPO) and peroxidases (POD) (Vamos-Vigyazo, 1981). It is therefore likely that enzymatic browning and tissue necrosis limit the capacity of Agrobacterium to infect the cot-node and transfer its T-DNA. Inhibitors of PPO and POD, such as cysteine and other sulfhydryl compounds, are routinely used to reduce enzymatic browning in food processing (Vamos-Vigyazo, 1981; Nicolas et al., 1994; Walker and Ferrar, 1998). However, very little research has been focused on implementing the use of inhibitors of PPO and POD to increase Agrobacterium-mediated T-DNA transfer in plant transformation systems (Perl et al., 1996; Enríguez-Obregón et al., 1999).

This is the first report of using the sulfhydryl-containing amino acid, cysteine, as an inhibitor of enzymatic browning to increase the frequency of Agrobacterium-mediated T-DNA delivery into the cot-node cells of soybean explants. Cysteine treatment made the cot-node explant more susceptible to Agrobacterium and therefore more amenable for transformation. It is possible that other sulfhydryl compounds may be more efficacious than cysteine. Other inhibitors of PPO and POD, such as D-cysteine, glutathione, dithiothreitol (DTT), and sodium thiosulfate, also increased Agrobacterium-mediated T-DNA delivery into cot-node cells (see Example III). Thus, it is possible that further research into inhibition of explant wound and pathogen responses may lead to even greater increases in Agrobacterium-mediated T-DNA delivery. Increased T-DNA delivery combined with improvements in the other steps of the transformation system will likely increase the efficiency for production of transgenic soybean plants using the cot-node method.

EXAMPLE III

The positive affect cysteine has on Agrobacterium-mediated T-DNA transfer occurs during the 5-day incubation on solid co-cultivation media. There are no increases detected when cysteine is amended solely to either the liquid YEP or liquid co-cultivation medium. This suggests that the plant explant is interacting with cysteine either alone or with Agrobacterium. To determine whether the response to cysteine is due to a nutritional gain (cysteine acting as an amino acid) in the medium or another factor, D-cysteine was amended to the solid co-cultivation media. The results of this experiment showed that both L- and D-cysteine increase GUS$^+$ foci at both the 5-day and 28-day interval in an analogous manner. Cysteine, therefore, is not increasing T-DNA transfer through medium enrichment.

Cysteine is known decrease enzymatic browning on wounded plant tissues by inhibiting enzymes active in plant defense mechanisms through its sulfhydryl group. Two such enzymes are polyphenol oxidase (PPO) and peroxidase (POD). PPO, or catecholase, is a copper metalloprotein, which can be inactivated by copper chelators or reducing agents. The POD protein contains ferriprotorphyrin III (hematin) as a prosthetic group, which can be inactivated by iron chelators or reducing agents. Other methods of reducing enzymatic browning include the use of sulfites, sulfur amino acids and sulfhydryl compounds, acidulents, and phenolic adsorbents, among others. Several of these agents were amended to the solid co-cultivation media to determine if T-DNA delivery was increased, as measured by the amount of GUS$^+$ sectors on explants after the 5-day incubation (Table 1).

TABLE 1

| Compounds Used | Concentration (g/l), unless otherwise indicated |
|---|---|
| PVPP | 5, 10, 15 |
| Ascorbic Acid | 0.05, 0.1, 0.15, 0.2, 0.3 |
| PVP | 5, 10, 20, 30 |
| DTT | 1, (0.75, 1.0, 1.25, 1.5, 2 mM) |
| Glutathione | 0.4 |
| Methionine | 0.050, 0.300, 1.0 |
| Cystathione | (0.0005, 0.001, 0.005, 0.01, 0.05, 0.1, 0.5, 1, 2 mM) |
| Bathocuproine disulfonic acid | (0.001, 0.005, 0.01, 0.05, 0.1, 0.5, 1, 1, 10, 15 mM) |
| Bathophenanthroline disulfonic acid | (0.001, 0.005, 0.01, 0.05, 0.1, 0.5, 1, 1, 10, 15 mM) |
| EDTA disodium | 0.05 |
| L-cystine | 0.1, 0.2, 0.3, 0.4, 1 |
| Ethionine | (0.1, 0.25, 0.75, 1.0, 1.25 mM) |
| Na-thiosulfate | (0.1, 1, 2, 5, 10, 20 mM) |
| Na-bisulfite | (0.01, 0.1, 1, 2, 5, 10, 20 mM) |
| Alanine | 0.4, 0.8 |
| D-cysteine | 0.4, 0.8 |
| L-cysteine | 0.05, 0.1, 0.2, 0.3, 0.4, 0.6, 0.8, 1.0, 1.5, 2.0 |

The explants from the cultivar 'Bert' were wounded as described hereinabove, inoculated with the Agrobacterium strain LBA4404 carrying the plasmid, pTOK233, and stained with GUS histochemical stain after co-cultivation. Of the components tested, increases in GUS$^+$ staining were found using glutathione, dithiothreitol, sodium thiosulfate, cysteine, bathocuproine disulfonic acid, and bathophenanthroline disulfonic acid (Table 2).

TABLE 2

| Other inhibitors: | YES | NO |
|---|---|---|
| PVPP | | X |
| PVP | | X |
| Ascorbic acid | | X |
| Methionine | | X |
| Cystathione | | X |
| EDTA disodium | | X |
| Ethionine | | X |
| Na-bisulfite | | X |
| Alanine | | X |
| DTT | X | |
| Glutathione | X | |
| Cystine | X | |
| Na-thiosulfate | X | |
| Metal Chelators: | | |
| Bathophenanthroline disulfonic acid | X | |
| Bathocuproline disulfonic acid | X | |

The fact that some compounds did not result in an increase in GUS$^+$ staining does not necessarily mean it is ineffective; the proper concentration may not have been tested. Scores were determined for the appearance of GUS$^+$ staining on groups of explants that responded to a given treatment (FIG. 12). The experiments using the two metal chelators, bathocuproline and bathophenanthroline, were designed to measure a range of iron or copper metals: from the addition of chelators, to no added metal, to a significant addition of each metal. The presence of bathocuproline significantly increased GUS$^+$ staining, reached almost no infection at 0 mM Cu, then increased slightly when copper was added once more. GUS$^+$ staining was only seen to peak in the bathophenanthroline treatment with the addition of the chelator at 0.05–0.005 mM, with no increase seen with additional iron. Many of these compounds scored as high as the cysteine (400 mg/l) control, suggesting cysteine may be increasing T-DNA transfer by reducing enzymatic browning and tissue necrosis.

REFERENCES

Ainley et al., *Plant Mol. Biol.,* 14, 949 (1990).
Back et al., *Plant Mol. Biol.,* 17, 9 (1991).
Bevan et al., *Nucl. Acid Res.,* 11, 369 (1983).
Bidney et al., *Plant Mol. Biol.,* 18, 301 (1992).
Bolton et al., *Science,* 232, 983 (1986).
Bouchez et al., *EMBO J.,* 8, 4197 (1989).
Boue et al., *J. Agric. Food Chem.,* 48, 2167 (2000).
Bustos et al., *EMBO J.,* 10, 1469 (1991).
Byrne et al., *Plant Cell Tissue Organ Cult.,* 8, 3 (1987).
Callis et al., *Genes Develop.,* 1, 1183 (1987).
Castresana et al., *EMBO J.,* 7, 1929 (1988).
Chandler et al., *The Plant Cell,* 1, 1175 (1989).
Chee et al., *Plant Physiol.,* 91, 1212 (1989).
Cho et al., *Planta,* 210, 195 (2000).
Christou et al., *Proc. Natl. Acad. Sci. USA* 84, 3962 (1987).
Christou et al., *Proc. Natl. Acad. Sci. USA,* 86, 7500 (1989).
Christou et al., *Tibtech* 8, 145 (1990).
Clemente et al., *Crop Sci.,* 40, 797 (2000).
Conkling et al., *Plant Physiol.,* 93, 1203 (1990).
Coruzzi et al., *EMBO J.,* 3, 1671 (1971).
DeBlaire et al., *Meth. Enz.,* 153, 277 (1987).

Dellaporta et al., in *Chromosome Structure and Function*, pp. 263–282 (1988).
Delzer et al., *Crop Sci.*, 30, 320 (1990).
Di et al., *Plant Cell Rep.*, 15, 746 (1996).
Ditta et al., *Proc. Natl. Acad. Sci. USA*, 77, 7347 (1980).
Doyle et al., *J. Biol. Chem.*, 261, 9228 (1986).
Dye et al., *Biochimie*, 79, 3 (1997).
Ebert et al., *PNAS USA*, 84, 5745 (1987).
Enríguez-Obregón et al., *Plant Cell Tissue Organ Cult.*, 59, 159 (1999).
Feinbaum et al., *Mol. Gen. Genet.*, 226, 449 (1991).
Finer et al., *In Vitro Cell. Dev. Biol.*, (1991)
Fraley et al., *Proc. Natl. Acad. Sci USA.*, 80, 4803 (1983).
Fromm et al., *The Plant Cell*, 1, 977 (1989).
Fry et al., *Plant Cell Reports*, 6, 321 (1987).
Gallie et al., *The Plant Cell*, 1, 301 (1989).
Gamborg et al., *Exp. Cell Res.*, 50, 151 (1968).
Guerrero et al., *Plant Molecular Biology*, 15, 11 (1990).
Hansen et al., *Proc. Natl. Acad. Sci. USA*, 91, 7603 (1994).
Heijne et al., *Eur. J. Biochem.*, 180, 535 (1989).
Hiei et al., *The Plant J.*, 6, 271 (1994).
Hinchee et al., *Bio/Technology*, 6, 915 (1988).
Hinchee et al., In: *Plant Cell and Tissue Culture*, Vasil and Thorpe (eds., Kiuwer Academic Publishers, Netherlands (1994).
Hoskin, *USDA Econ. Res.*, 1I 35 (1987).
Hudspeth et al., *Plant Mol. Biol.*, 12, 579 (1989).
Ikuta et al., *Biotech.*, 8, 241 (1990).
Jefferson et al., *EMBO* 6, 3901 (1987).
Jefferson, *Plant Molecular Biology Reporter*, 5, 387 (1987).
Joshi, *Nucl. Acid Res.*, 15, 6643 (1987).
Kares et al., *Plant Mol. Biol.*, 15, 905 (1990).
Kartha et al., *Can. J. Bot.*, 59, 1671 (1981).
Katz et al., *J. Gen. Microbiol.*, 129, 2703 (1983).
Keegstra et al., *Ann. Rev. Plant Physiol. Plant Mol. Biol.*, 40, 471 (1989).
Keller et al., *EMBO J.*, 8, 1309 (1989).
Knutzon et al., *Proc. Natl. Acad. Sci USA*, 89, 2624 (1992).
Komatsuda et al., *Crop. Sci.*, 31, 333 (1991).
Kridl et al., *Seed Sci. Res.*, 1, 209 (1991).
Kuhlemeier et al., *Plant Cell*, 1, 471 (1989).
Lam and Chua, *Science*, 248, 471 (1990).
Lam and Chua, *J. Biol. Chem.*, 266, 17131 (1991).
Lawton et al., *Plant Mol. Biol.*, 9, 31F (1987).
Lin et al., *Plant Physiol.*, 84, 856 (1987).
Liu et al., *In Vitro Cell. Dev. Biol.*, 28, 153 (1992).
McCabe et al., *Biotechnology*, 6, 923 (1988).
McElroy et al., *Molec. Gen. Genet.*, 231, 150 (1991).
McElroy et al., *Plant Cell*, 2, 163 (1990).
*Methods in Enzymology*, 153, 292 (1987).
Meurer et al., *Plant Cell Rep.*, 18, 180 (1998).
Molvig et al., *Proc. Natl. Acad. Sci. USA*, 94, 8393 (1997).
Moore et al., *Plant Cells Reports* (1994).
Murakami et al., *Mol. Gen. Genet.*, 205, 42 (1986).
Murishige and Skoog, *Physiol. Plant*, 15, 473 (1962).
Nicolas et al., *CRC Crit. Rev. Food Sci. Nutr.*, 34, 109 (1994).
Niedz et al., *Plant Cell Reports*, 14, 403 (1995).
Odell et al., *Nature*, 313, 810 (1985).
Olhoft and Phillips, In: *Plant responses to environmental stresses: from phytohormones to genome reorganization*, Lerner, H. R., ed., M. Dekker Inc., NY, 111–148 (1999).
Ou-Lee et al., *Proc. Natl. Acad. Sci USA*, 83, 6815 (1986).
Ow et al., *Science*, 234, 856 (1986).
Padgette et al., *Herbicide Resistant Crops: Agricultural, Environmental, Economic, Regulatory, and Technical Aspects*. S. O. Duke (Ed.), CRC Press, p. 53 (1996).
Parrott et al., *Plant Cell Rep.*, 7, 615 (1989).
Parrott et al., *In Vitro Cell. Dev. Biol.* (1994).
Pawlowski et al., *Mol. Biotechnol.*, 6, 17 (1996).
Perl et al., *Nature Biotech.*, 14, 624 (1998).
Potrykus et al., *Mol. Gen. Genet.*, 199, 183 (1985).
Potrykus, *Trends Biotech.*, 7, 269 (1989).
Powell et al., *Heredity*, 58, 75 (1987).
Prasher et al., *Biochem. Biophys. Res. Comm.*, 126, 1259 (1985).
Radke et al., *Theor. Appl. Genet.*, 75, 685 (1988).
Richins et al., *NAR*, 20, 8451 (1987).
Rogers et al., *Meth. Enz.*, 118, 627 (1986).
Rogers et al., *Meth. Enz.*, 153, 253 (1987a).
Rogers, et al., In: *Plant Gene Research—Plant DNA Infectious Agents*, Springer-Verlag, Wien, N Y. (1997b).
Santarem et al., *Plant Cell Rep.*, 17, 752 (1998).
Sato et al., *Plant Cell Reports*, (1993).
Sambrook et al., *Molecular Cloning: A Laboratory Manual*, Cold Spring Harbor, NY (1989).
Schulze-Lefert et al., *EMBO J.*, 8, 651 (1989).
Sengupta-Gopalan, *Proc. Natl. Acad. Sci. USA* 82, 3320 (1985).
Shah et al., *Science*, 233, 478 (1986).
Skriver et al., *Plant Cell*, 2, 503 (1990).
Slighton and Beachy, *Planta*, 172, 356 (1987).
Smith and Huyser, *USDA Econ. Res.*, 1, 22 (1987).
Stalker et al., *Science*, 242, 419 (1988).
Stark et al., *Science*, 258, 287 (1992).
Stayton et al., *Aust. J. Plant. Physiol.*, 18, 507 (1991).
Steart et al., *Plant Physiol.* (1996).
Steifel et al., *The Plant Cell*, 2, 785 (1990).
Sullivan et al., *Mol. Gen. Genet.*, 215, 431 (1989).
Sutcliffe, *PNAS USA* 75, 3737 (1978).
Thillet et al., *J. Biol. Chem.*, 263, 12500 (1988).
Torisky et al., *Plant Cell Rep.*, 17, 102 (1997).
Trick et al., *Plant Tissue Cult. Biotechnol.*, 3, 9 (1997).
Twell et al., *Plant Physiol.*, 91, 1270 (1989).
Vámos-Vigyázó, *CRC Crit. Rev. Food Sci. Nutr.*, 15, 49 (1981).
Vasil et al., *Plant Physiol.*, 91, 5175 (1989).
Walker et al., *PNAS USA*, 84, 6624 (1987).
Walker and Ferrar, *Biotechnol. Gen. Eng. Rev.*, 15, 457 (1998).
Wang et al., *Proceedings First Intern. Symp. Soybean in Tropical and Subtropical Countries*, (1983).
Wang et al., *Mol. Cell. Biol.*, 12, 3399 (1992).
Wayne et al., *Plant Mol. Biol.*, (1988).
Weisshaar et al., *EMBO J.*, 10, 1777 (1991).
Yamaguchi-Shinozaki et al., *Plant Mol. Biol.*, 15, 905 (1990).
Yeh et al., *J. Agric. Assoc. China*, 40, 77 (1991).
Yang et al., *PNAS USA*, 87, 4144 (1990).
Zambryski et al., *Cell*, 56, 193 (1989).
Zhang et al., *Plant Cell Tissue and Organ Culture*, 56, 37 (1999).
Zukowsky et al., *PNAS USA*, 80, 1101 (1983).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for stable transformation of leguminous plant tissue or cells, comprising:

a) contacting leguminous plant tissue or cells with an Agrobacterium comprising a recombinant DNA and one or more sulfhydryl-containing agents which one or more agents are present in solid media in an amount effective to enhance the stable transformation of the leguminous plant tissue or cells relative to corresponding plant tissue or cells contacted with the Agrobacterium in the absence of the one or more agents, wherein the plant tissue or cells are embryogenic somatic cells, immature embryo, meristem, or a cotyledon explant, and wherein the stable transformation is enhanced by at least 0.5%; and b) identifying stably transformed plant tissue or cells.

2. The method of claim 1 wherein the stable transformation is enhanced by at least 10%.

3. The method of claim 1 wherein the stable transformation is enhanced by at least 5-fold.

4. The method of claim 1 wherein the transformed tissue or cells are identified by selection.

5. The method of claim 4 wherein the transformed tissue or cells are selected for with hygromycin.

6. The method of claim 1 wherein a cotyledon explant is contacted with the Agrobacterium.

7. The method of claim 6 wherein the cotyledon is wounded in or near the axillary bud or cotyledonary node prior to contacting.

8. The method of claim 6 wherein the cotyledon explant is from a legume seedling.

9. The method of claim 1 further comprising regenerating a differentiated transformed plant from the stably transformed plant tissue or cells.

10. The method of claim 1 wherein one agent is cysteine.

11. The method of claim 10 wherein cysteine is present at 50 mg/L to 2000 mg/L.

12. The method of claim 1 wherein one agent is glutathione, sodium thiosulfate, or dithiothreitol.

13. The method of claim 12 wherein glutathione is present at 0.4 g/L or 0.001 to 1 mM, sodium thiosulfate is present at 0.1 to 20 mM, or dithiothreitol is present at 1 g/L or 0.75 to 2 mM.

14. The method of claim 1 wherein the plant tissue or cells are from soybean.

15. The method of claim 1 wherein the recombinant DNA comprises a selectable marker.

16. The method of claim 1 wherein the recombinant DNA comprises a detectable marker.

17. The method of claim 1 wherein the recombinant DNA comprises a promoter operably linked to an open reading frame of interest.

* * * * *

UNITED STATES PATENT AND TRADEMARK OFFICE
CERTIFICATE OF CORRECTION

PATENT NO. : 6,759,573 B2
DATED : July 6, 2004
INVENTOR(S) : Olhoft et al.

It is certified that error appears in the above-identified patent and that said Letters Patent is hereby corrected as shown below:

Title page,
Item [56], References Cited, FOREIGN PATENT DOCUMENTS, after "12/1998" insert -- A01N --.
OTHER PUBLICATIONS,
"Bolton, G.W., et al.," reference, delete "tumefaciensLoci" and insert -- tumefaciens Loci --, therefor.
"Enriquez-Obregon, G.A., et al.," reference, delete "Culuture" and insert -- Culture --, therefor.

Signed and Sealed this

Twenty-first Day of December, 2004

JON W. DUDAS
*Director of the United States Patent and Trademark Office*